(12) United States Patent
Back et al.

(10) Patent No.: US 10,660,959 B2
(45) Date of Patent: *May 26, 2020

(54) FORMULATIONS OF A PI3K/MTOR-INHIBITOR FOR INTRAVENOUS ADMINISTRATION

(71) Applicant: Pfizer Inc., New York, NY (US)

(72) Inventors: Kevin Richard Back, Sandwich (GB); Michael Cram, Sandwich (GB); Aidan James Harper, Sandwich (GB); W. James Huang, New York, NY (US); Jonathan Richard Lillis, Sandwich (GB); Timothy Michael Lukas, Sandwich (GB); Sumit Luthra, New York, NY (US)

(73) Assignee: Pfizer Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/189,009

(22) Filed: Nov. 13, 2018

(65) Prior Publication Data

US 2019/0105390 A1    Apr. 11, 2019

Related U.S. Application Data

(62) Division of application No. 15/534,999, filed as application No. PCT/IB2015/059515 on Dec. 10, 2015, now Pat. No. 10,172,942.

(60) Provisional application No. 62/250,633, filed on Nov. 4, 2015, provisional application No. 62/093,060, filed on Dec. 17, 2014.

(51) Int. Cl.
| | | |
|---|---|---|
| *A61K 47/12* | (2006.01) | |
| *C07D 401/12* | (2006.01) | |
| *A61K 9/00* | (2006.01) | |
| *A61K 47/26* | (2006.01) | |
| *A61K 9/08* | (2006.01) | |
| *A61K 9/19* | (2006.01) | |
| *A61K 31/5377* | (2006.01) | |
| *A61K 47/02* | (2006.01) | |

(52) U.S. Cl.
CPC .......... *A61K 47/12* (2013.01); *A61K 9/0019* (2013.01); *A61K 9/08* (2013.01); *A61K 9/19* (2013.01); *A61K 31/5377* (2013.01); *A61K 47/02* (2013.01); *A61K 47/26* (2013.01); *C07D 401/12* (2013.01); *C07B 2200/13* (2013.01)

(58) Field of Classification Search
CPC ...... A61K 47/12; A61K 9/0019; A61K 47/26; A61K 9/108; A61K 9/19; A61K 31/5377; A61K 47/02; C07D 401/12; C07B 2200/13

See application file for complete search history.

(56) References Cited

U.S. PATENT DOCUMENTS

| | | |
|---|---|---|
| 2014/0248274 A1 | 9/2014 | Kallmeyer |
| 2015/0258102 A1 | 9/2015 | Bagrodia |

FOREIGN PATENT DOCUMENTS

| | | |
|---|---|---|
| WO | 2009143313 A1 | 11/2009 |
| WO | 2010096619 A1 | 8/2010 |

OTHER PUBLICATIONS

Chen et al., "Quantifying amorphous content of lactose using parallel beam X-ray powder diffraction and whole pattern fitting", Journal of Pharmaceutical and Biomedical Analysis, 2001, 26, 63-72.
Venkatesan et al., "Bis(morpholino-1,3,5-triazine) Derivatives: Potent Adenosine 5'-Triphosphate Competitive Phosphatidylinositol-3-kinase/Mammalian Target of Rapamycin Inhibitors: Discovery of Compound 26 (PKI-587), a Highly Efficacious Dual Inhibitor", J. Med. Chem., 2010, 53, 2636-2645.
International Search Report dated Feb. 16, 2016, for PCT/IB2015/059515, filed on Dec. 10, 2015. (6 pages).
Written Opinion of the International Searching Authority dated Aug. 8, 2016, for PCT/IB2015/059515, filed on Dec. 10, 2015. (6 pages).
Kumar et al., "Formulation and Evaluation of Lyophilized Antibacterial Agent", International Journal of PharmTech Research, 5(4) 1581-1589 2013.

*Primary Examiner* — Shirley V Gembeh
(74) *Attorney, Agent, or Firm* — David Rubin

(57) ABSTRACT

The present invention relates to a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a pharmaceutically acceptable salt thereof, that is a clear solution. Such a formulation is particularly suitable for intravenous or parenteral administration to a patient.

10 Claims, 3 Drawing Sheets

PXRD pattern of the crystalline form of 1-(4-{[4-(dimethylamino)piperidin-1-yl]carbonyl}phenyl)-3-[4-(4,6-dimorpholin-4-yl-1,3,5-triazin-2-yl)phenyl]urea L-lactate from Example 4, Preparation A re. European Pharmacopoeia Method 2.9.20: "*Figure 2.9.20.-1. – Apparatus for visible particles*"

Chromatogram of Blank Solution (Diluent) at Full Scale

Expanded Chromatogram of Blank Solution (Diluent)

NOTE: Chromatogram solvent peak and system peak can be instrument dependent.

FORMULATIONS OF A PI3K/MTOR-INHIBITOR FOR INTRAVENOUS ADMINISTRATION

This Application is a divisional application from U.S. application Ser. No. 15/534,999, filed Jun. 9, 2017, allowed on Aug. 15, 2018, which claims the benefit of national stage filing under 35 U.S.C. 371 of Patent Cooperation Treaty Patent Application No. PCT/IB2015/059515, filed Dec. 10, 2015, which claims the benefit of U.S. Provisional Application No. 62/250,633 filed Nov. 4, 2015 and U.S. Provisional Application No. 62/093,060 filed on Dec. 17, 2014, the contents of each of which are hereby incorporated by reference in their entirety.

The present invention relates to a pharmaceutical formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a pharmaceutically acceptable salt thereof. More specifically, the present invention relates to a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a pharmaceutically acceptable salt thereof, that is a clear solution. Such a formulation is particularly suitable for intravenous administration to a patient.

1-(4-{[4-(Dimethylamino)piperidin-1-yl]carbonyl}phenyl)-3-[4-(4,6-dimorpholin-4-yl-1,3,5-triazin-2-yl)phenyl]urea, and preparations thereof, are disclosed in WO2009/143313. The compound is an inhibitor of PI3 kinase and mTOR that is useful for the treatment of cancer.

A crystalline form of 1-(4-{[4-(dimethylamino)piperidin-1-yl]carbonyl}phenyl)-3-[4-(4,6-dimorpholin-4-yl-1,3,5-triazin-2-yl)phenyl]urea, and process for the preparation thereof, are disclosed in WO2010/096619.

1-(4-{[4-(Dimethylamino)piperidin-1-yl]carbonyl}phenyl)-3-[4-(4,6-dimorpholin-4-yl-1,3,5-triazin-2-yl)phenyl]urea has the chemical structure:

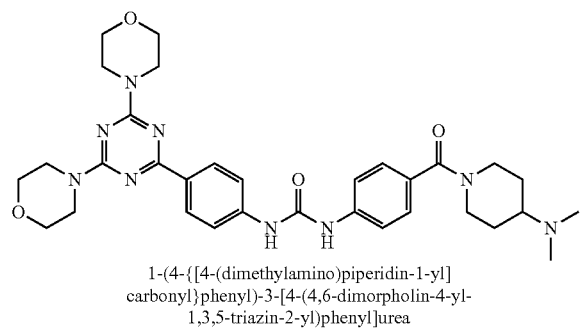 [SMILES: CN(C)C1CCN(C(=O)c2ccc(NC(=O)Nc3ccc(-c4nc(N5CCOCC5)nc(N5CCOCC5)n4)cc3)cc2)CC1]

1-(4-{[4-(dimethylamino)piperidin-1-yl]carbonyl}phenyl)-3-[4-(4,6-dimorpholin-4-yl-1,3,5-triazin-2-yl)phenyl]urea 1-(4-{[4-(Dimethylamino)piperidin-1-yl]carbonyl}phenyl)-3-[4-(4,6-dimorpholin-4-yl-1,3,5-triazin-2-yl)phenyl]urea may be prepared in crystalline form and is chemically and physically stable at 25° C. and 60% Relative Humidity (RH) for up to 3 years in this form. However, this free base is insufficiently water soluble to allow the preparation of an aqueous solution formulation suitable for intravenous or parenteral administration at the therapeutic dosage levels required.

There is a need to develop a pharmaceutically acceptable formulation of 1-(4-{[4-(dimethylamino)piperidin-1-yl]carbonyl}phenyl)-3-[4-(4,6-dimorpholin-4-yl-1,3,5-triazin-2-yl)phenyl]urea that is (a) chemically stable on storage (e.g. at 25° C. and 60% RH), and/or (b) that will facilitate effective intravenous (or parenteral) administration of the drug to a mammal, including a human being.

Preferably, the formulation is suitable for intravenous administration of 1-(4-{[4-(dimethylamino)piperidin-1-yl]carbonyl}phenyl)-3-[4-(4,6-dimorpholin-4-yl-1,3,5-triazin-2-yl)phenyl]urea in view of the particular pharmacokinetic and bioavailability characteristics of this drug.

It is essential that an intravenous formulation of any drug is a solution to facilitate safe and effective administration to a patient. It must be particle-free, and not form a gel or suspension. A clear, aqueous solution is preferred.

A clear solution is defined as a visually clear solution essentially free from any visible particulates that can be observed on a visual inspection. Generally, if any particulate matter is observed, the formulation is not suitable for intravenous administration and should not be utilised as occlusion of blood vessels may occur. Accordingly, in view of the qualitative nature of the visual test, the term "essentially free from any visible particulates" is usually applied when no visible particulate matter is observed.

Particulate matter may be defined as follows:
speck—discrete particle whose shape cannot be determined without magnification
smoke or swirl—fine particles that look like smoke or a tornado and usually originate from the sample vial floor and twist upward as the vial is swirled
flocculent material—loosely aggregated particles or soft flakes
particulates with a definite shape or characteristic can be described as glass-like, metallic-looking, etc.

The visual inspection can be conducted in accordance with the method defined in European Pharmacopoeia Method 2.9.20 entitled "Particulate contamination: visible particles". This method determines particulate contamination of injections and infusions by extraneous, mobile, undissolved particles, other than gas bubbles, that may be present in the solutions. The test is intended to provide a simple procedure for the visual assessment of the quality of parenteral solutions as regards visible particles. Other validated methods may be also be used.

In European Pharmacopoeia Method 2.9.20 the apparatus (see "FIG. 2.9.20.-1" shown in FIG. 2) consists of a viewing station comprising:
a matt black panel of appropriate size held in a vertical position
a non-glare white panel of appropriate size held in a vertical position next to the black panel
an adjustable lampholder fitted with a suitable, shaded, white-light source and with a suitable light diffuser (a viewing illuminator containing two 13 Watt fluorescent tubes, each 525 mm in length, is suitable). The intensity of illumination at the viewing point is maintained between 2000 lux and 3750 lux, although higher values are preferable for coloured glass and plastic containers.

The Method states: "Remove any adherent labels from the container and wash and dry the outside. Gently swirl or invert the container, ensuring that air bubbles are not introduced, and observe for about 5 seconds in front of the white panel. Repeat the procedure in front of the black panel. Record the presence of any particles."

It has now been surprisingly found that the technical problem has been solved by a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid and water, wherein 1-(4-{[4-(dimethylamino)piperidin-1-yl]carbonyl}phenyl)-

3-[4-(4,6-dimorpholin-4-yl-1,3,5-triazin-2-yl)phenyl]urea is present at a solution concentration of less than 6 mg/ml and sufficient lactic acid is present to provide a clear solution; or 1-(4-{[4-(dimethylamino)piperidin-1-yl]carbonyl}phenyl)-3-[4-(4,6-dimorpholin-4-yl-1,3,5-triazin-2-yl)phenyl]urea, or a phosphate salt thereof, orthophosphoric acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 4 mg/ml and sufficient orthophosphoric acid is present to provide a clear solution (hereafter "the formulation of the invention").

Such a formulation can be directly administered to the patient (in order to avoid degradation occurring), intravenously or parenterally, preferably with the addition of a tonicity modifier. Alternatively, for administration to a patient at a later date, such a formulation, optionally containing a bulking agent and/or tonicity modifier, may be first freeze-dried to prepare a lyophilised solid composition that is chemically stable on storage for preferably at least 2 years, and which lyophilised solid composition then can be constituted, or reconstituted, to provide a clear aqueous solution, preferably with the addition of a tonicity modifier, as necessary, immediately prior to administration to a patient by the intravenous (or parenteral) route.

It has been found that the use of alternative acids to the lactic acid or orthophosphoric acid used in the formulation of the invention, at the preferred concentration of from 2.5-5.5 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea, results in cloudy formulations containing particulate matter or which gel, and does not lead to the essentially clear, particle-free solutions required for intravenous (or parenteral) administration to a patient.

In respect of the formulations comprising lactic acid:

it has been found that at solution concentrations of 1-(4-{[4-(dimethylamino)piperidin-1-yl]carbonyl}phenyl)-3-[4-(4,6-dimorpholin-4-yl-1,3,5-triazin-2-yl)phenyl]urea of 6 mg/ml or above, the necessary clear solutions at the pH required for intravenous administration to a patient are not obtained, or are not obtained consistently.

preferably the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 6 mg/ml and sufficient lactic acid is present to provide a clear solution.

the concentration of 1-(4-{[4-(dimethylamino)piperidin-1-yl]carbonyl}phenyl)-3-[4-(4,6-dimorpholin-4-yl-1,3,5-triazin-2-yl)phenyl]urea in the formulation of the invention may be from 1 to 5.5 mg/ml, from 2 to 5.5 mg/ml, or from 3 to 5.5 mg/ml (calculated as the named free base).

preferably, the invention provides a pharmaceutical aqueous solution formulation wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 2.5 to 5.5 mg/ml.

preferably, the invention provides a pharmaceutical aqueous solution formulation wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of about 5 mg/ml.

preferably, when the free base of 1-(4-{[4-(dimethylamino)piperidin-1-yl]carbonyl}phenyl)-3-[4-(4,6-dimorpholin-4-yl-1,3,5-triazin-2-yl)phenyl]urea is used, above 2.5 mole equivalents of lactic acid are present in the formulation of the invention. More preferably, from 3 to 10, from above 2.5 to 8.0, or from 3.5 to 4.5 mole equivalents of lactic acid are present in the formulation of the invention. Most preferably, about 4.1 mole equivalents of lactic acid are present in the formulation of the invention.

preferably, when the free base of 1-(4-{[4-(dimethylamino)piperidin-1-yl]carbonyl}phenyl)-3-[4-(4,6-dimorpholin-4-yl-1,3,5-triazin-2-yl)phenyl]urea is used, the invention provides a pharmaceutical aqueous solution formulation wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 5.0 to 5.5 mg/ml and at least 2.5 mole equivalents of lactic acid are present.

preferably, when the free base of 1-(4-{[4-(dimethylamino)piperidin-1-yl]carbonyl}phenyl)-3-[4-(4,6-dimorpholin-4-yl-1,3,5-triazin-2-yl)phenyl]urea is used, the invention provides a pharmaceutical aqueous solution formulation wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of about 5 mg/ml and at least 2.5 mole equivalents of lactic acid are present.

preferably, when the free base of 1-(4-{[4-(dimethylamino)piperidin-1-yl]carbonyl}phenyl)-3-[4-(4,6-dimorpholin-4-yl-1,3,5-triazin-2-yl)phenyl]urea is used, the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of about 5 mg/ml, and at least 2.5 mole equivalents of lactic acid are present and in an amount sufficient to ensure a clear solution is formed.

it should be noted that 1-(4-{[4-(dimethylamino)piperidin-1-yl]carbonyl}phenyl)-3-[4-(4,6-dimorpholin-4-yl-1,3,5-triazin-2-yl)phenyl]urea forms a 1:1 (mole equivalent) lactate salt with lactic acid. The formulation of the invention may be prepared using the 1-(4-{[4-(dimethylamino)piperidin-1-yl]carbonyl}phenyl)-3-[4-(4,6-dimorpholin-4-yl-1,3,5-triazin-2-yl)phenyl]urea free base or using a lactic acid salt of 1-(4-{[4-(dimethylamino)piperidin-1-yl]carbonyl}phenyl)-3-[4-(4,6-dimorpholin-4-yl-1,3,5-triazin-2-yl)phenyl]urea. When the lactic acid salt is used, preferably above 1.5 mole equivalents of lactic acid are used to achieve the presence of the preferred lower limit of above 2.5 mole equivalents of lactic acid in the formulation of the invention.

preferably, the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea lactate, lactic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of about 5 mg/ml, and at least 1.5 mole equivalents of lactic acid are present and in an amount sufficient to ensure a clear solution is formed.

DL-lactic acid, D-lactic acid or L-lactic acid, or any combination thereof, may be used in the formulation of the invention. Preferably, DL-lactic acid is used.

preferably, the pH of the formulation of the invention is not greater than 3.7. More preferably, the pH of the formulation of the invention is from 3.0 to 3.7, from 3.3 to 3.6, or from 3.4 to 3.5.

in a preferred embodiment, the present invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of up to 5.5 mg/ml, and above 2.5 mole equivalents of lactic acid are present and in an amount sufficient to ensure a clear solution is formed with a pH of no greater than 3.7.

in a preferred embodiment, the present invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, lactic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of about 5 mg/ml, and about 4.1 mole equivalents of lactic acid are present and in an amount sufficient to ensure a clear solution is formed with a pH of no greater than 3.7.

a crystalline form of 1-(4-{[4-(dimethylamino)piperidin-1-yl]carbonyl}phenyl)-3-[4-(4,6-dimorpholin-4-yl-1,3,5-triazin-2-yl)phenyl]urea L-lactate may be used to prepare the formulation of the invention. Preferably, the crystalline form of 1-(4-{[4-(dimethylamino)piperidin-1-yl]carbonyl}phenyl)-3-[4-(4,6-dimorpholin-4-yl-1,3,5-triazin-2-yl)phenyl]urea L-lactate used has a PXRD pattern (measured using a Bruker D4 diffractometer and copper K-alpha radiation) with major peaks at about 16.2, 17.3, 18.4, 18.9, 19.9, 20.9 and 23.1 degrees 2-theta (±0.2 degrees 2-theta). This crystalline form of 1-(4-{[4-(dimethylamino)piperidin-1-yl]carbonyl}phenyl)-3-[4-(4,6-dimorpholin-4-yl-1,3,5-triazin-2-yl)phenyl]urea L-lactate is distinguished from other known forms of this salt by having characterizing peaks at about 6.5, 15.9, 20.9, 22.1 and 23.1 degrees 2-theta (±0.2 degrees 2-theta).

In respect of the formulations comprising orthophosphoric acid:

preferably, the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, orthophosphoric acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 4 mg/ml and sufficient orthophosphoric acid is present to provide a clear solution.

preferably, the invention provides a pharmaceutical aqueous solution formulation wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 3.0 to 3.5 mg/ml.

preferably, the invention provides a pharmaceutical aqueous solution formulation wherein at least 5 mole equivalents of orthophosphoric acid are used.

preferably, the invention provides a pharmaceutical aqueous solution formulation wherein from 5 to 7 mole equivalents of orthophosphoric acid are used.

in a preferred embodiment the present invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, orthophosphoric acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 4 mg/ml, from 5 to 7 mole equivalents of orthophophoric acid are present and in an amount sufficient to ensure a clear solution is formed.

preferably, the pH of the formulation prepared is from 2-2.5 prior to intravenous administration. The pH is then preferably adjusted to from 3.0-4.5 for intravenous administration.

if a phosphate salt of 1-(4-{[4-(dimethylamino)piperidin-1-yl]carbonyl}phenyl)-3-[4-(4,6-dimorpholin-4-yl-1,3,5-triazin-2-yl)phenyl]urea is used, this is preferably prepared using orthophosphoric acid.

If the formulation of the invention is to be freeze-dried to provide a lyophilised solid composition, a bulking agent is preferably added to the formulation prior to the freeze-drying process commencing. The primary function of the bulking agent is to provide the freeze-dried solid with a non-collapsible, structural integrity that will allow rapid reconstitution on constitution of the aqueous formulation prior to administration, and it should also facilitate efficient lyophilisation. Bulking agents are typically used when the total mass of solutes in the formulation is less than 2 g/100 ml. Bulking agents may also be added to achieve isotonicity with blood. The bulking agent may be selected from a saccharide, sugar alcohol, amino acid or polymer, or be a mixture of two or more of any thereof. Preferably, the bulking agent is a sugar or sugar alcohol, or a mixture thereof. Preferably, the sugar is sucrose. Preferably, the sugar alcohol is mannitol.

Reconstitution of the lyophilized solid composition may be achieved by addition of the requisite quantity of water that was present prior to lyophilisation in order that a clear solution is obtained. A tonicity modifier may then be added prior to use.

Constitution of the lyophilized solid composition may be achieved using an appropriate quantity of water and/or an aqueous solution of a suitable tonicity modifier in order to ensure that a clear solution is obtained.

A tonicity modifier must be present prior to intravenous or parenteral administration of the formulation to a patient by injection to avoid crenation or hemolysis of red blood cells, and to mitigate or avoid pain and discomfort to the patient. This requires that the formulation to be administered to the patient has an effective osmotic pressure that is approximately the same as that of the blood of the patient.

Suitable tonicity modifiers are non-ionic tonicity modifiers such as glycerol, sorbitol, mannitol, sucrose, propylene glycol or dextrose, or a mixture of any 2 or more thereof. Preferably the non-ionic tonicity modifier is dextrose, sucrose or mannitol, or is a mixture of any 2 or more thereof.

Aqueous pharmaceutical formulations that are suitable for intravenous administration generally have a pH of from 3 to 9. The formulations of the invention that are to be intravenously administered preferably have a pH of from 3 to 4.5.

The formulation of the invention may be used for the curative, palliative or prophylactic treatment of cancer in a mammal, including a human being. The cancer to be treated may be selected from the group consisting of leukemia, skin cancer, bladder cancer, breast cancer, uterus cancer, ovary cancer, prostate cancer, lung cancer, colon cancer, pancreas cancer, renal cancer, gastric cancer and brain cancer.

The weekly dose of 1-(4-{[4-(dimethylamino)piperidin-1-yl]carbonyl}phenyl)-3-[4-(4,6-dimorpholin-4-yl-1,3,5-triazin-2-yl)phenyl]urea to be administered by the intravenous route for the treatment of cancer using the formulations disclosed herein is preferably in the range of from 100-400 mg/ml per week.

Figure 1:
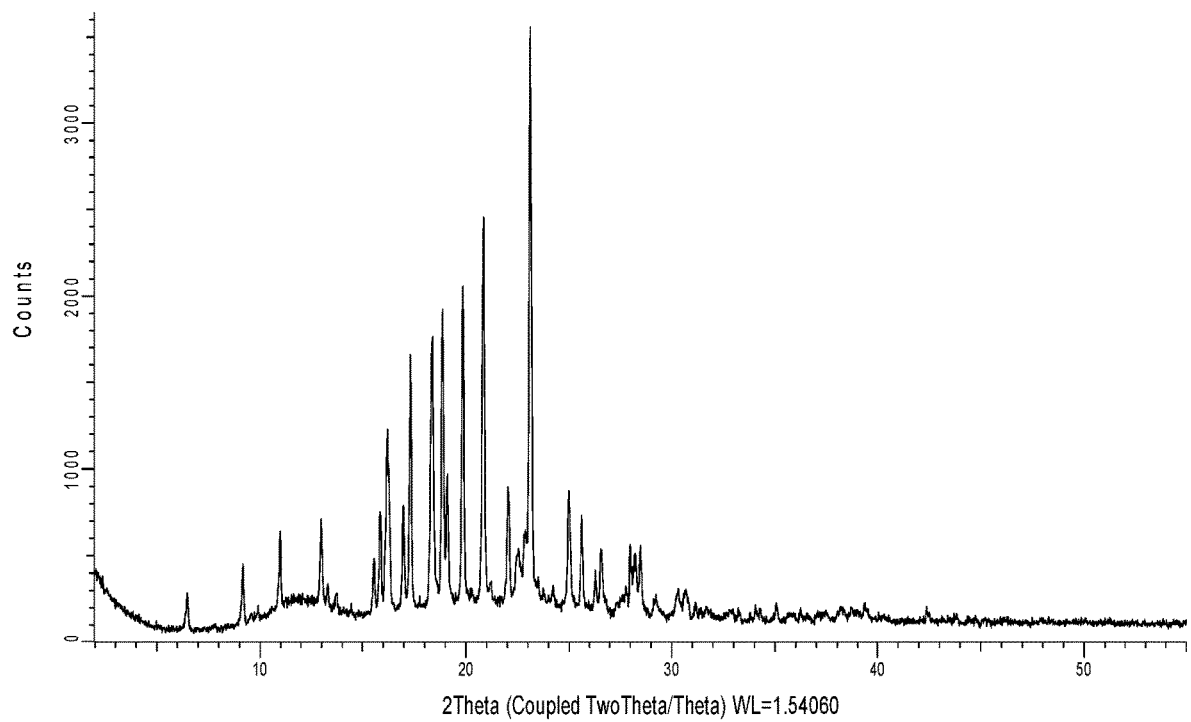
FIG. 1 shows the PXRD pattern of the crystalline form of 1-(4-{[4-(dimethylamino)piperidin-1-yl]carbonyl}phenyl)-3-[4-(4,6-dimorpholin-4-yl-1,3,5-triazin-2-yl)phenyl]urea L-lactate, as prepared Example 4, Preparation A.
Figure 2:
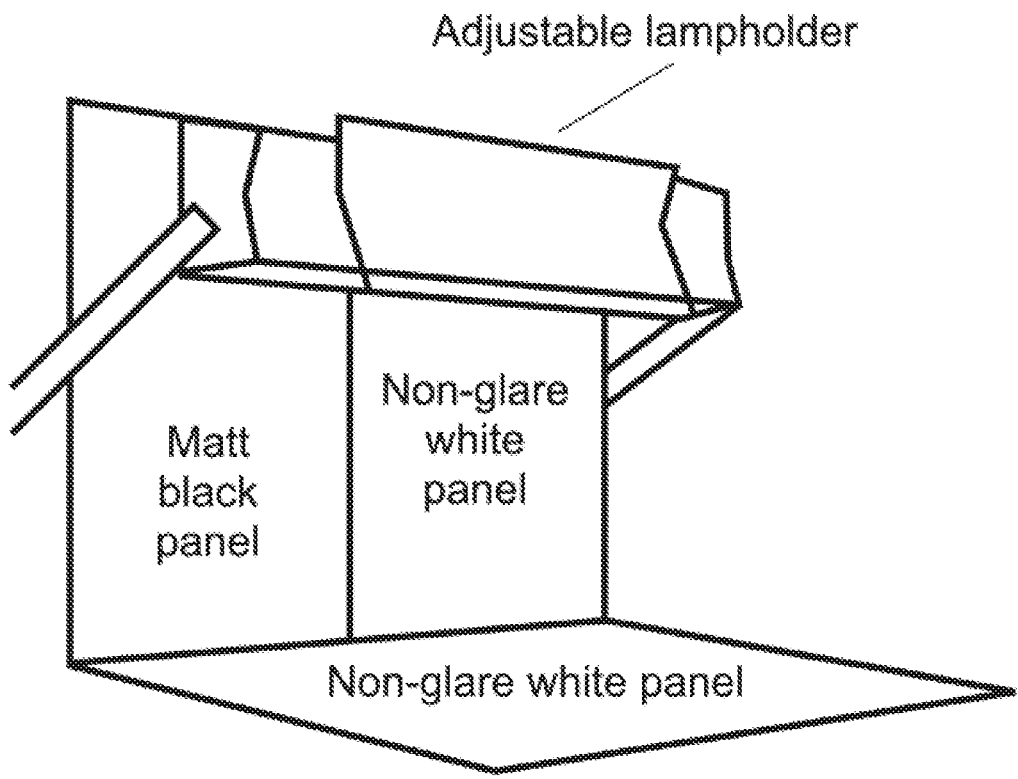
FIG. 2 reproduces FIG. 2.9.20.-1 from European Pharmacopoeia Method 2.9.20.

The following Examples illustrate the preparation of the formulations of the invention.

EXAMPLES

Example 1

Preparation of a Pharmaceutical Aqueous Solution Formulation Comprising 5 mg/ml 1-(4-{[4-(dimethylamino)piperidin-1-yl]carbonyl}phenyl)-3-[4-(4,6-dimorpholin-4-yl-1,3,5-triazin-2-yl)phenyl]urea and DL-lactic acid D,L-lactic acid (334 mg) was dissolved in water for irrigation to make a solution with a total volume of 100 ml. 1-(4-{[4-(Dimethylamino)piperidin-1-yl]carbonyl}phenyl)-3-[4-(4,6-dimorpholin-4-yl-1,3,5-triazin-2-yl)phenyl]urea (200 mg) was dissolved in 37 ml of this lactic acid solution, mixing with an Ultra Turrax T25 (trade mark) homogeniser for 120 minutes and sonicating the solution for 10 minutes in an ultrasonic bath. The mixture was then stirred overnight with a magnetic stirrer to provide a clear solution. This was made up to 40 ml volume with the lactic acid solution using a volumetric flask. The solution was filtered using a 0.2 µm nylon filter into a clean 50 ml vial in a laminar air flow (LAF) cabinet. The first 5 ml of filtered solution was used to wet the filter and was discarded as unrepresentative of the filtered solution. The vial was crimped and sealed using clean lyo-stoppers and flip-off caps. The solution was inspected visually and was found to be a clear, colourless solution.

Example 2

Preparation of (a) a 5 mg/ml Pharmaceutical Aqueous Solution Formulation Comprising 1-(4-{[4-(dimethylamino)piperidin-1-yl]carbonyl}phenyl)-3-[4-(4,6-dimorpholin-4-yl-1,3,5-triazin-2-yl)phenyl] urea, DL-lactic acid and mannitol; and (b) Preparation of a Lyophilised Solid Composition Thereof (a) 36,100 g of water for injection was weighed into a vessel. 125.82 g of DL-Lactic acid (90.6% purity, parenteral grade) was slowly added and the mixture was stirred until the lactic acid dissolved. 195.3 g of 1-(4-{[4-(dimethylamino)piperidin-1-yl]carbonyl}phenyl)-3-[4-(4,6-dimorpholin-4-yl-1,3,5-triazin-2-yl)phenyl]urea was slowly added and the mixture was stirred until the material dissolved. 1900 g of mannitol powder (parenteral) was gradually added and the mixture was stirred until the material dissolved. Water for injection was added to make the solution up to a total weight of 38,760 g and the solution was stirred for a further 10 minutes. The pH was checked and found to be 3.4 with a solution temperature of 29.3° C. The solution was sterile filtered through an in-line 0.45 µm clarification filter and 0.22 µm filter assembly. This solution was then filled into 50 mL vials with a target fill volume of 20.8 mL for each vial. The vials were each partially stoppered (not sealed) with a 20 mm Gray Lyo D777-1 V10-F597W FluroTec Siliconised (trade mark) stopper.

(b) These vials were then loaded into stainless steel trays and inserted into a LSL1000 (trade mark) freeze dryer. The shelf temperature was set at 5° C. The freeze drying cycle was run using the method below.

| Treatment | Step | Rate/Hold | Temperature (° C.) | Time (min) | Pressure mbar (Pascals) |
|---|---|---|---|---|---|
| Loading | | | 5 | | atmospheric |
| Stabilisation | 1 | hold | 5 | 120 | atmospheric |
| Freezing | 2 | rate | −25 | 300 | atmospheric |
| | 3 | hold | −25 | 180 | atmospheric |
| | 4 | rate | −12 | 130 | atmospheric |
| | 5 | hold | −12 | 180 | atmospheric |
| | 6 | rate | −40 | 93 | atmospheric |
| | 7 | hold | −40 | 240 | atmospheric |
| | 8 | hold | −40 | 60 | atmospheric |
| Evacuation | 9 | hold | −40 | 30 | 0.200 (20) |
| Primary Drying | 10 | rate | 10 | 100 | 0.200 (20) |
| | 11 | hold | 10 | 1440 | 0.200 (20) |
| Secondary Drying | 12 | rate | 40 | 60 | 0.200 (20) |
| | 13 | hold | 40 | 360 | 0.200 (20) |
| | 14 | rate | 25 | 30 | 0.200 (20) |
| | 15 | hold | 25 | 30 | 0.200 (20) |
| | 16 | rate | 25 | 10 | 0.200 (20) |

The freeze dryer was back-filled with sterile filtered nitrogen to a set point of ca. 700 mbar (70,000 Pascals), and the vials were fully closed using the stoppers. The freeze dryer was then vented to atmospheric pressure using sterile filtered air and the vials were unloaded from the freeze dryer.

Each vial contained the freeze dried (lyophilised) formulation as a white solid.

Example 3

Reconstitution of a 5 mg/ml Pharmaceutical Aqueous Solution Formulation Comprising 1-(4-{[4-(dimethylamino)piperidin-1-yl]carbonyl}phenyl)-3-[4-(4,6-dimorpholin-4-yl-1,3,5-triazin-2-yl)phenyl]urea, DL-lactic acid and mannitol from a Lyophilised Solid Composition The vials of lyophilised solid composition samples prepared in Example 2(b) were reconstituted as follows.

Approximately 25 ml of water for injection was placed into a syringe and a 0.2 micron PVDF filter membrane was attached to the syringe. Approximately 5 ml of the water was filtered through the membrane and discarded. 20 ml of the water remaining in the syringe was then filtered into the 50 ml vial containing the lyophilised composition as prepared in Example 2(b). The mixture was swirled in the vial until a clear, colourless solution was achieved.

The reconstituted solution was analysed as follows:

(a) pH

The pH of the solution in the vial was measured as pH=3.52 at 23.2 degrees ° C.

(b) Visual Appearance of Reconstituted Solution

One of the reconstituted vials was visually inspected using a method based on that of European Pharmacopoeia Method 2.9.20 described above. The method is designed to observe the presence of any visible particles.

By this method the solution in the vial was visually inspected in a Verivide DCAC60 (trade mark) light cabinet using a light meter reading of 3250 lux against a matt black panel and a white panel.

The result showed a clear, colourless solution, free from particulate matter, had been achieved on reconstitution.

(c) Analysis for Sub-Visible Particles

The solution in the vial was assessed for the presence of sub-visible particles using a HIAC apparatus (trade mark) by using a sub-visible particulate determination method that is based on that defined in United States Pharmacopoeia 36 <788> Method 1 ("Light Obscuration Particle Count Test"). In order for a solution to be suitable for parenteral or intravenous administration the results must comply with the criteria for "Test 1.B" for USP 36 <788> Method 1 as these define the widest possible acceptable limits for sub-visible particulate matter. This Test states as follows:

"Test 1.B (Solutions for parenteral infusion or solutions for injection supplied in containers with a nominal content of less than 100 mL)—The preparation complies with the test if the average number of particles present in the units tested does not exceed 6000 per container equal to or greater than 10 µm and does not exceed 600 per container equal to or greater than 25 µm".

By this method, firstly, 10 vial solution samples were pooled. Four samples of not less than 5 mL each were removed from the pooled solution and, for each sample, the number of particles equal to or greater than 10 µm and 25 µm were counted using a HIAC HRLD 400 (trade mark) sensor. The result obtained for the first sample was disregarded. For each of the remaining three samples, the mean number of particles per container was calculated and compared with the requirements of USP 36 <788> Test 1.B. These samples each met the acceptance criteria of USP 36 <788> Test 1.B for a solution to be suitable for parenteral or intravenous administration

Example 4

Preparation of a Crystalline form of 1-(4-{[4-(dimethylamino)piperidin-1-yl]carbonyl}phenyl)-3-[4-(4, 6-dimorpholin-4-yl-1,3,5-triazin-2-yl)phenyl]urea L-lactate Preparation A:

1-(4-{[4-(Dimethylamino)piperidin-1-yl]carbonyl}phenyl)-3-[4-(4,6-dimorpholin-4-yl-1,3,5-triazin-2-yl)phenyl]urea (52 mg) was weighed into a 2 ml vial. A 22 mg/ml solution of L-lactic acid in 98:2 v/v ethyl acetate:dimethylformamide (0.5 ml) was added to the vial. This slurry was stirred at about 23° C. for 24 hours. The slurry was then filtered through a 0.2 µm nylon centrifuge filter to isolate the crystalline title compound.

The product was analysed by PXRD (see "Investigation 7" below) using a Bruker D4 (trade mark) diffractometer and copper K-alpha radiation and gave a pattern that is shown in FIG. 1.

Preparation B:

1-(4-{[4-(Dimethylamino)piperidin-1-yl]carbonyl}phenyl)-3-[4-(4,6-dimorpholin-4-yl-1,3,5-triazin-2-yl)phenyl]urea (52 mg) was weighed into a 2 ml vial. A 22 mg/ml solution of L-lactic acid in 98:2 v/v ethyl acetate:dimethylformamide (0.5 ml) was added to the vial. The slurry was heated to 60° C. at a rate of 5° C./minute, held at 60° C. for 20 min. and then cooled at 0.1° C./minute to 5° C. where it was held until it was isolated (24 hours after the start of the heating step). The slurry was filtered through a 0.2 µm nylon centrifuge filter to isolate the crystalline title compound.

The product was analysed by PXRD (see "Investigation 7" below) using a Bruker D4 diffractometer and copper K-alpha radiation and gave a pattern consistent with that shown in FIG. 1.

The following investigations were conducted in respect of the present invention.

INVESTIGATIONS

1. Investigation Regarding 3 mg/ml Aqueous Formulations of 1-(4-{[4-(dimethylamino)piperidin-1-yl]carbonyl}phenyl)-3-[4-(4,6-dimorpholin-4-yl-1,3,5-triazin-2-yl)phenyl]urea with Various Acids Procedure Nine individual acidic buffer solutions were prepared as follows in order to use ca. 6.8 mole equivalents of each acid (except where indicated):

| Buffer (Buffer Number) | Method |
| --- | --- |
| 33.3 mM Citric Acid at pH 2.94 (1) | 5.47772 g of Citric Acid Anhydrous was added to approximately 75 mL of WFI. 1.42293 g of Sodium Citrate Dihydrate was added to this solution. This was then made to 1 L volume in a volumetric flask using WFI. pH was then recorded. |
| 33.3 mM Succinic Acid at pH 2.77 (2) | 0.39386 g of Succinic Acid was added to approximately 80 mL of WFI. This was then made to 100 mL volume in a volumetric flask using WFI. pH was then recorded. |
| 33.3 mM Acetic Acid at pH 3.25 (3) | 1.96522 g of Glacial Acetic Acid was added to approximately 75 mL of WFI. 0.077013 g of Sodium Acetate Trihydrate was added to this solution. This was then made to 1 L volume in a volumetric flask using WFI. pH was then recorded. |

-continued

| Buffer (Buffer Number) | Method |
| --- | --- |
| 33.3 mM orthophosphoric Acid at pH 1.91 (4) | 3.26683 g of Orthophosphoric Acid was added to approximately 500 mL of WFI. This was then made to 1 L volume in a volumetric flask using WFI. pH was then recorded. |
| 33.3 mM Glycine at pH 6.06 (5) | 2.50191 g of Glycine was added to approximately 500 mL of WFI. This was then made to 1 L volume in a volumetric flask using WFI. pH was then recorded. |
| 33.3 mM Tartaric Acid at pH 2.22 (6) | 0.50018 g of Tartaric Acid was added to approximately 75 mL of WFI. This was then made to 100 mL volume in a volumetric flask using WFI. pH was then recorded. |
| 43 mM DL-Lactic Acid at pH 2.47 (7) (in order to use 8.8 mole equivalents of acid) | 0.43090 g of Racemic Mixture DL Lactic Acid* was dissolved in approximately 75 mL of WFI. This was then made to 100 mL volume in a volumetric flask using WFI. pH was then recorded. |
| 33.3 mM Maleic Acid at pH 1.79 (8) | 0.38864 g of Maleic Acid was dissolved in approximately 75 mL of WFI. This was then made up to 100 mL volume in a volumetric flask using WFI. pH was then recorded. |
| 33.3 mM Malic Acid at pH 2.46 (9) | 0.44667 g of Malic Acid was dissolved in approximately 75 mL of WFI. This was then made to 100 mL volume in a volumetric flask using WFI. pH was then recorded. |
| 33 mM DL-Lactic Acid at pH 2.60 (10) | 0.33915 g of Racemic Mixture DL Lactic Acid* was dispensed into a 100 mL volumetric flask and made up to volume using WFI. pH was then recorded. |

(WFI = water for irrigation)
(*90% w/w DL-Lactic acid in water)

The stability testing was conducted using three ca. 3 mg/ml samples of 1-(4-{[4-(dimethylamino)piperidin-1-yl]carbonyl}phenyl)-3-[4-(4,6-dimorpholin-4-yl-1,3,5-triazin-2-yl)phenyl]urea for each acid buffer prepared above. These samples were prepared using a target weight of 1-(4-{[4-(dimethylamino)piperidin-1-yl]carbonyl}phenyl)-3-[4-(4,6-dimorpholin-4-yl-1,3,5-triazin-2-yl)phenyl]urea of 15.45 mg (due to 97.1% API Activity) by weighing the required quantity into each vial as follows:

| Buffer Number (see above) | N = 1 | N = 2 | N = 3 |
| --- | --- | --- | --- |
| 1 | 15.38 mg | 15.52 mg | 15.35 mg |
| 2 | 15.65 mg | 15.40 mg | 15.28 mg |
| 3 | 15.69 mg | 15.36 mg | 15.47 mg |
| 4 | 15.67 mg | 15.48 mg | 15.41 mg |
| 5 | 15.54 mg | 15.33 mg | 15.58 mg |
| 6 | 15.93 mg | 15.35 mg | 15.50 mg |
| 7 | 15.74 mg | 15.33 mg | 15.33 mg |
| 8 | 15.79 mg | 15.75 mg | 15.33 mg |
| 9 | 15.36 mg | 15.58 mg | 15.42 mg |
| 10 | 15.33 mg | 15.43 mg | 15.32 mg |

5 mL of the respective buffer was introduced to the weighed sample in the vials and the vials were each closed by a crimped cap then sealed with a protective film. The vials were placed on a roller bed in an oven at 25° C. for 5 days.

Results

At the end of the 5 day period the pH of each sample was measured and a visual observation of each sample was made using a light box as described in European Pharmacopoeia Method 2.9.20 (above), inspecting the samples against a black and a white background. The sample was also tested by illumination using a narrow (Tyndall) beam light source and then visually inspected from a direction perpendicular to the light beam in order to identify undissolved solid particles.

Six vials were found to have fallen off the roller during the course of the experiment meaning the exact time those vials actually rolled is unknown. These samples are marked in the "pH results" and "visual observations" tables below with an asterix (*).

pH Results After 5 Days at 25° C.

| Buffer number | N = 1 | N = 2 | N = 3 |
| --- | --- | --- | --- |
| 1 (Citric Acid) | 3.02 | 3.01 | 3.01 |
| 2 (Succinic Acid) | 3.14 | 3.14 | 3.15 |
| 3 (Acetic Acid) | 3.86 | 3.87 | 3.88 |
| 4 (Orthophosphoric Acid) | 2.01 | 2.07 | 2.04 |
| 5 (Glycine) | 6.45 | 6.71 | 6.51 |
| 6 (Tartaric Acid) | 2.54* | 2.37* | 2.38* |
| 7 (DL-Lactic Acid) | 2.91* | 2.91 | 2.91 |
| 8 (Maleic Acid) | 1.91 | 1.87* | 1.90 |
| 9 (Malic Acid) | 2.71 | 2.70* | 2.70 |
| 10 (DL-Lactic Acid) | 3.07 | 3.21 | 3.27 |

Visual Observations of Samples After 5 Days at 25° C.

| Buffer number | N = 1 | N = 2 | N = 3 |
| --- | --- | --- | --- |
| 1 (Citric Acid) | Haze | Haze | Haze |
| 2 (Succinic Acid) | Haze | Haze | Haze |
| 3 (Acetic Acid) | Not in Solution | Not in Solution | Not in Solution |
| 4 (Ortho-phosphoric Acid) | Haze | Clear | Haze |
| 5 (Glycine) | Not in Solution | Not in Solution | Not in Solution |
| 6 (Tartaric Acid) | Haze* | Haze* | Haze* |
| 7 (DL - Lactic Acid) | Clear* | Clear | Clear |
| 8 (Maleic Acid) | Haze | Haze* | Haze |
| 9 (Malic Acid) | Haze | Haze* | Haze |
| 10 (DL-Lactic Acid) | Clear | Clear | Clear |

Conclusion

The results show that the 3 mg/ml samples containing 1-(4-{[4-(dimethylamino)piperidin-1-yl]carbonyl}phenyl)-3-[4-(4,6-dimorpholin-4-yl-1,3,5-triazin-2-yl)phenyl]urea and DL—lactic acid achieved a clear solution after 5 days at 25° C. All the other samples except one (orthophosphoric acid-N=2 sample) failed to achieve a clear solution. As such, acids other than DL-lactic acid and orthophosphoric acid would not be suitable for the preparation of pharmaceutical aqueous solution formulations for intravenous administration to a patient at a required API (active pharmaceutical ingredient) concentration.

2. Investigation Regarding 3 mg/ml and 4 mg/ml Aqueous Formulations of 1-(4-{[4-(dimethylamino)piperidin-1-yl]carbonyl}phenyl)-3-[4-(4,6-dimorpholin-4-yl-1,3,5-triazin-2-yl)phenyl]urea with Various Acids Procedure (a) Four individual acidic buffer solutions were prepared as follows for use in the 3 mg/ml formulations, in order to use ca. 6.8 mole equivalents of the respective acid:

| Buffer | Method |
|---|---|
| 33.3 mM Hydrochloric Acid at pH 1.51 | 6.7 mL of 1M aqueous HCl was dispensed using a positive displacement pipette into a 200 mL volumetric flask, this was then made to volume with WFI and then using a positive displacement pipette, an extra 1 mL of WFI was added to reach the correct molarity. The pH was then recorded. |
| 33.3 mM (D)-Lactic Acid at pH 2.68 | 100 mg of (D)-Lactic Acid was dissolved in 33.3 mL of WFI in a volumetric flask. The pH was then recorded. |
| 33.3 mM (L)-Lactic Acid at pH 2.72 | 153.65 mg of (L)-Lactic Acid was dissolved in 40 mL of WFI. This was then poured into a 50 mL volumetric flask and made to volume using WFI. The pH was then recorded. |
| 33.3 mM Orthophosphoric Acid at pH 1.87 | 0.16909 g of Orthophosphoric Acid was added to approximately 40 mL of WFI. This was then made to 50 mL volume in a volumetric flask using WFI. The pH was then recorded. |

(WFI = water for irrigation)

The stability testing was conducted using three ca. 3 mg/ml samples of 1-(4-{[4-(dimethylamino)piperidin-1-yl]carbonyl}phenyl)-3-[4-(4,6-dimorpholin-4-yl-1,3,5-triazin-2-yl)phenyl]urea for each acid buffer prepared above. These samples were prepared using a target weight of 1-(4-{[4-(dimethylamino)piperidin-1-yl]carbonyl}phenyl)-3-[4-(4,6-dimorpholin-4-yl-1,3,5-triazin-2-yl)phenyl]urea of 15.45 mg (due to 97.1% API Activity) by weighing the required quantity into each vial as follows:

| Buffer | N = 1 | N = 2 | N = 3 |
|---|---|---|---|
| Hydrochloric acid | 15.71 | 15.34 | 15.95 |
| (D)-Lactic acid | 15.52 | 15.40 | 15.50 |
| (L)-Lactic acid | 15.22 | 15.80 | 15.30 |
| Orthophosphoric Acid | 15.43 mg | 15.50 mg | 15.79 mg |

(b) Individual acidic buffer solutions were prepared as follows for use in the 4 mg/ml formulations, in order to use ca. 5.1 mole equivalents of the respective acid (except where indicated):

| Buffer (Buffer Number) | Method |
|---|---|
| 33.3 mM Citric Acid at pH 2.98 (1) | 0.27346 g of Citric Acid Anhydrous was dissolved in approximately 40 mL of WFI. 0.07284 g of Sodium Citrate Dihydrate was also added to this solution. This was then dispensed into a 50 mL volumetric flask and made to volume using WFI. pH was then recorded. |
| 33.3 mM Succinic Acid at pH 2.79 (2) | 0.20084 g of Succinic Acid was dissolved in approximately 40 mL of WFI. This was dispensed into a 50 mL volumetric flask and made to volume using WFI. pH was then recorded. |
| 33.3 mM Acetic Acid at pH 3.35 (3) | 0.1021 g of Glacial Acetic Acid was dissolved in approximately 40 mL of WFI. 0.00528 g of Sodium Acetate Trihydrate was also added to this solution. This was then dispensed into a 50 mL volumetric flask and made to volume using WFI. pH was then recorded. |
| 33.3 mM Orthophosphoric Acid at pH 1.87 (4) | 0.16909 g of Orthophosphoric Acid was dissolved in approximately 40 mL of WFI. This was then dispensed into a 50 mL volumetric flask and made to volume using WFI. pH was then recorded. |
| 33.3 mM Tartaric Acid at pH 2.28 (5) | 0.25180 g of (D)-Tartaric Acid was dissolved in approximately 40 mL of WFI. This was then dispensed into a 50 mL volumetric flask and made to volume using WFI. pH was then recorded. |
| 33.3 mM Hydrochloric Acid at pH 1.51 (6) | 6.7 mL of 1M aqueous HCl was dispensed using a positive displacement pipette into a 200 mL volumetric flask, this was then made to volume with WFI and then using a positive displacement pipette, an extra 1 mL of WFI was added to reach the correct molarity. The pH was then recorded. |
| 43 mM (DL)-Lactic Acid at pH 2.53 (7) (in order to use 6.6 mole equivalents of acid) | 0.21400 g of (DL)-Lactic Acid* was dissolved in approximately 40 mL of WFI. This was then dispensed into a 50 mL volumetric flask and made to volume using WFI. pH was then recorded. |
| 3.5 mM Maleic Acid at pH 2.55 (8) (in order to use 0.5 mole equivalents of acid) | 0.02057 g of Maleic Acid was dissolved in approximately 40 mL of WFI. This was then dispensed into a 50 mL volumetric flask and made to volume using WFI. pH was then recorded. |
| 3.5 mM Malic Acid at pH 3.08 (9) (in order to use 0.5 mole equivalents of acid) | 0.02357 g of Malic Acid was dissolved in approximately 40 mL of WFI. This was then dispensed into a 50 mL volumetric flask and was made to volume using WFI. pH was then recorded. |
| 33.3 mM (D)-Lactic Acid at pH 2.68 (10) | 100 mg of (D)-Lactic Acid was dissolved in 33.3 mL of WFI in a volumetric flask. pH was then recorded. |
| 33.3 mM (L)-Lactic Acid at pH 2.72 (11) | 153.65 mg of (L)-Lactic Acid was dissolved in 40 mL of WFI. This was then poured into a 50 mL volumetric flask and made to volume using WFI. pH was then recorded. |
| 33.3 mM (DL)-Lactic Acid at pH 2.60 (12) | 0.33915 g of (DL)-Lactic Acid* was dispensed into a 100 mL volumetric flask. This was then made to 100 mL volume with WFI. pH was then recorded. |
| 33.3 mM Maleic Acid at pH 1.72 (13) | 0.19385 g of Maleic Acid was added to approximately 40 mL of WFI. This was poured into a 50 mL Volumetric flask then made to volume with WFI. pH was then recorded. |
| 33.3 mM Malic Acid at pH 2.30 (14) | 0.22332 g of Malic Acid was added to approximately 40 mL of WFI. This was poured into a 50 mL Volumetric flask then made to volume with WFI. pH was then recorded. |

(WFI = water for irrigation)
(*90% w/w DL-Lactic acid in water)

The stability testing was conducted using three ca. 4 mg/ml samples of 1-(4-{[4-(dimethylamino)piperidin-1-yl]carbonyl}phenyl)-3-[4-(4,6-dimorpholin-4-yl-1,3,5-triazin-2-yl)phenyl]urea for each acid buffer prepared above. These samples were prepared using a target weight of 1-(4-{[4-(dimethylamino)piperidin-1-yl]carbonyl}phenyl)-3-[4-(4,6-dimorpholin-4-yl-1,3,5-triazin-2-yl)phenyl]urea of 20.60 mg (due to 97.1% API Activity) by weighing the required quantity into each vial as follows:

| Buffer number | N = 1 | N = 2 | N = 3 |
|---|---|---|---|
| 1 | 20.53 | 21.09 | 20.71 |
| 2 | 20.72 | 20.54 | 20.87 |
| 3 | 20.55 | 20.79 | 20.43 |
| 4 | 20.91 | 20.97 | 20.81 |
| 5 | 20.07 | 20.73 | 20.59 |
| 6 | 20.97 | 20.29 | 20.14 |
| 7 | 20.95 | 20.65 | 20.45 |
| 8 | 20.93 | 20.21 | 20.81 |
| 9 | 20.29 | 20.25 | 20.48 |

| Buffer number | N = 1 | N = 2 | N = 3 |
| --- | --- | --- | --- |
| 10 | 20.37 | 20.66 | 20.50 |
| 11 | 20.90 | 20.18 | 20.52 |
| 12 | 20.53 | 20.43 | 20.75 |
| 13 | 20.79 | 20.69 | 20.44 |
| 14 | 20.55 | 20.87 | 20.55 |

For the formulations of both (a) and (b) above, 5 mL of the respective buffer was introduced to the weighed sample in the vial and the vials were each closed by a crimped cap and sealed with a protective film. The vials were placed on a roller bed in an oven at 25° C. for 5 days.

Results le;.4qAt the end of the 5 day period the pH of each sample was measured and a visual observation of each sample was made using a light box as described in European Pharmacopoeia Method 2.9.20 (above), inspecting the samples against a black and a white background. The sample was also tested by illumination using a narrow (Tyndall) beam light source and then visually inspected from a direction perpendicular to the light beam in order to identify undissolved solid particles.

pH After 5 Days at 25° C.

3 mg/mL

| Buffer | Initial pH | N = 1 | N = 2 | N = 3 |
| --- | --- | --- | --- | --- |
| 33.3 mM Hydrochloric Acid | 1.51 | 1.56 | 1.56 | 1.55 |
| 33.3 mM (D)-Lactic Acid | 2.68 | 3.14 | 3.07 | 3.09 |
| 33.3 mM (L)-Lactic Acid | 2.72 | 3.17 | 3.13 | 3.14 |
| 33.3 mM Ortho-phosphoric Acid | 1.87 | 2.09 | 2.18 | 2.18 |

4 mg/mL

| Buffer | Initial pH | N = 1 | N = 2 | N = 3 |
| --- | --- | --- | --- | --- |
| 33.3 mM Citric Acid | 2.98 | 3.07 | 3.09 | 3.08 |
| 33.3 mM Succinic Acid | 2.79 | 3.19 | 3.17 | 3.15 |
| 33.3 mM Acetic Acid | 3.35 | 4.07 | 4.09 | 4.08 |
| 33.3 mM Orthophosphoric Acid | 1.87 | 2.09 | 2.06 | 2.05 |
| 33.3 mM Tartaric Acid | 2.28 | 2.41 | 2.42 | 2.42 |
| 33.3 mM Hydrochloric Acid | 1.51 | 1.63 | 1.62 | 1.65 |
| 43 mM (DL)-Lactic Acid | 2.53 | 3.07 | 3.05 | 3.04 |
| 3.5 mM Maleic Acid | 2.55 | 4.70 | 4.66 | 4.66 |
| 3.5 mM Malic Acid | 3.08 | 5.14 | 5.11 | 5.11 |
| 33.3 mM (D)-Lactic Acid | 2.68 | 3.27 | 3.31 | 3.34 |
| 33.3 mM (L)-Lactic Acid | 2.72 | 3.36 | 3.37 | 3.38 |
| 33.3 mM (DL)-Lactic Acid | 2.60 | 3.23 | 3.23 | 3.28 |
| 33.3 mM Maleic Acid | 1.72 | 2.03 | 2.04 | 2.05 |
| 33.3 mM Malic Acid | 2.30 | 2.70 | 2.74 | 2.73 |

Visual Observations of Samples After 5 Days at 25° C.

3 mg/mL

| Buffer | N = 1 | N = 2 | N = 3 |
| --- | --- | --- | --- |
| 33.3 mM Hydrochloric Acid | Haze Present | Haze Present | Haze Present |
| 33.3 mM (D)-Lactic Acid | Clear | Clear | Clear |
| 33.3 mM (L)-Lactic Acid | Clear | Clear | Clear |
| 33.3 mM Orthophosphoric Acid | Clear | Clear | Clear |

4 mg/mL

| Buffer | N = 1 | N = 2 | N = 3 |
| --- | --- | --- | --- |
| 33.3 mM Citric Acid | Haze Present | Haze Present | Haze Present |
| 33.3 mM Succinic Acid | Haze Present | Haze Present | Haze Present |
| 33.3 mM Acetic Acid | Not in Solution | Not in Solution | Not in Solution |
| 33.3 mM Orthophosphoric Acid | Gelling Occurred | Gelling Occurred | Gelling Occurred |
| 33.3 mM Tartaric Acid | Haze Present | Haze Present | Haze Present |
| 33.3 mM Hydrochloric Acid | Possible Gel/Haze Present | Possible Gel/Haze Present | Possible Gel/Haze Present |
| 43 mM (DL)-Lactic Acid | Clear | Clear | Clear |
| 3.5 mM Maleic Acid | Possible Gel/Haze Present | Possible Gel/Haze Present | Possible Gel/Haze Present |
| 3.5 mM Malic Acid | Haze Present | Haze Present | Haze Present |
| 33.3 mM (D)-Lactic Acid | Clear | Clear | Clear |
| 33.3 mM (L)-Lactic Acid | Clear | Clear | Clear |
| 33.3 mM (DL)-Lactic Acid | Clear | Clear | Clear |
| 33.3 mM Maleic Acid | Haze Present | Haze Present | Haze Present |
| 33.3 mM Malic Acid | Haze Present | Haze Present | Haze Present |

Conclusion

The results show that the 3 mg/ml and 4 mg/ml samples containing 1-(4-{[4-(dimethylamino)piperidin-1-yl]carbonyl}phenyl)-3-[4-(4,6-dimorpholin-4-yl-1,3,5-triazin-2-yl)phenyl]urea and D-lactic acid, L-lactic acid or DL-lactic acid achieved a clear solution after 5 days at 25° C.

The results show that the 3 mg/ml samples containing 1-(4-{[4-(dimethylamino)piperidin-1-yl]carbonyl}phenyl)-3-[4-(4,6-dimorpholin-4-yl-1,3,5-triazin-2-yl)phenyl]urea and orthophosphoric acid also achieved a clear solution after 5 days at 25° C.

All the other samples failed achieve a clear solution and acids other than DL-lactic acid, D-lactic acid, L-lactic acid and orthophosphoric acid would not be suitable for the preparation of pharmaceutical aqueous solution formulations for intravenous administration to a patient at a required API concentration.

3. Investigation Regarding Aqueous Formulations of 1-(4-{[4-(dimethylamino)piperidin-1-yl]carbonyl}phenyl)-3-[4-(4,6-dimorpholin-4-yl-1,3,5-triazin-2-yl)phenyl]urea with DL-lactic Acid at Varying pH and Concentration Procedure (a) Buffer solutions for use in the preparation of 3 mg/ml, 5 mg/ml, 5.5 mg/ml, 6 mg/ml and 6.5 mg/ml formulations of 1-(4-{[4-(dimethylamino)piperidin-1-yl]carbonyl}phenyl)-3-[4-(4,6-dimorpholin-4-yl-1,3,5-triazin-2-yl)phenyl]urea were prepared according to the following calculations (WFI=water for irrigation) (* 90% w/w DL-LACTIC ACID IN WATER).

3 mg/mL @0.9 Mole Equivalence at 10 mL Scale equals 4.39 mg of DL-Lactic Acid* in 10 mL WFI. (1)

3 mg/mL @2.25 Mole Equivalence at 10 mL Scale equals 10.98 mg of DL-Lactic Acid* in 10 mL WFI. (2)

3 mg/mL @3.7 Mole Equivalence at 10 mL Scale equals 17.99 mg of DL-Lactic Acid* in 10 mL WFI. (3)

5 mg/mL @0.9 Mole Equivalence at 10 mL Scale equals 7.32 mg of DL-Lactic Acid* in 10 mL WFI. (4)

5 mg/mL @2.25 Mole Equivalence at 10 mL Scale equals 18.29 mg of DL-Lactic Acid* in 10 mL WFI. (5)

5 mg/mL @3.7 Mole Equivalence at 10 mL Scale equals 30 mg of DL-Lactic Acid* in 10 mL WFI. (6)

5 mg/mL @7.2 Mole Equivalence at 10 mL Scale equals 58.54 mg of DL-Lactic Acid* in 10 mL WFI. (7)

5 mg/mL @10.8 Mole Equivalence at 10 mL Scale equals 87.80 mg of DL-Lactic Acid* in 10 mL WFI. (8)

5.5 mg/mL @2.25 Mole Equivalence at 10 mL Scale equals 20.12 mg of DL-Lactic Acid* in 10 mL WFI. (9)

5.5 mg/mL @3.7 Mole Equivalence at 10 mL Scale equals 33 mg of DL-Lactic Acid* in 10 mL WFI. (10)

5.5 mg/mL @10.8 Mole Equivalence at 10 mL Scale equals 96.58 mg of DL-Lactic Acid* in 10 mL WFI. (11)

6 mg/mL @3.7 Mole Equivalence at 10 mL Scale equals 36 mg of DL-Lactic Acid* in 10 mL WFI. (12)

6 mg/mL @3.7 Mole Equivalence at 20 mL Scale equals 72 mg of DL-Lactic Acid* in 20 mL WFI. (14)

6.5 mg/mL @3.7 Mole Equivalence at 10 mL Scale equals 39 mg of DL-Lactic Acid* in 10 mL WFI. (13)

6.5 mg/mL @3.7 Mole Equivalence at 20 mL Scale equals 78 mg of DL-Lactic Acid* in 10 mL WFI. (15)

The buffer solutions are prepared using WFI in 10 ml (*20 ml where indicated in the Table below) volumetric flasks using the following DL-lactic acid weights (**90% W/W DL-LACTIC ACID IN WATER):

| Buffer number | Weight** (mg) | Actual mole equivalence | pH |
|---|---|---|---|
| 1 | 3.91 | 0.8 | 3.14 |
| 2 | 12.12 | 2.5 | 2.86 |
| 3 | 18.16 | 3.7 | 2.69 |
| 4 | 6.97 | 0.9 | 2.99 |
| 5 | 19.07 | 2.3 | 2.68 |
| 6 | 30.80 | 3.8 | 2.55 |
| 7 | 57.10 | 7.0 | 2.41 |
| 8 | 87.82 | 10.8 | 2.30 |
| 9 | 20.36 | 2.3 | 2.67 |
| 10 | 33.37 | 3.7 | 2.56 |
| 11 | 100.33 | 11.2 | 2.27 |
| 12 | 35.93 | 3.6 | 2.55 |
| 13 | 41.84 | 3.9 | 2.50 |
| 14 | 70.9* | 3.6 | 2.50 |
| 15 | 78.6* | 3.7 | 2.45 |

(b) The following quantities of 1-(4-{[4-(dimethylamino)piperidin-1-yl]carbonyl}phenyl)-3-[4-(4,6-dimorpholin-4-yl-1,3,5-triazin-2-yl)phenyl]urea were weighed into vials (n.b. 1-(4-{[4-(dimethylamino)piperidin-1-yl]carbonyl}phenyl)-3-[4-(4,6-dimorpholin-4-yl-1,3,5-triazin-2-yl)phenyl]urea has an activity of 97.1% and the target weights below were corrected for this activity).

| re. Buffer number | Target Weight (mg) | Actual Weight (mg) |
|---|---|---|
| 1 | 15.45 | 15.53 |
| 2 | 15.45 | 15.52 |
| 3 | 15.45 | 15.57 |
| 4 | 25.75 | 25.68 |
| 5 | 25.75 | 25.70 |
| 6 | 25.75 | 25.76 |
| 7 | 25.75 | 25.82 |
| 8 | 25.75 | 25.77 |
| 9 | 28.32 | 28.38 |
| 10 | 28.32 | 28.41 |
| 11 | 28.32 | 28.34 |
| 12 | 30.90 | 31.22 |
| 13 | 33.47 | 33.61 |
| 14 | 30.90 | N = 1 30.83 |
|  |  | N = 2 30.98 |
|  |  | N = 3 30.81 |
| 15 | 33.47 | N = 1 33.49 |
|  |  | N = 2 33.35 |
|  |  | N = 3 33.38 |

5 mL of the corresponding DL-lactic acid buffer was added to the API in the vial and each vial was then closed with a crimped cap and sealed using protective film.

Samples 1-11 were placed on a roller bed at room temperature and at 50 rpm for ca. 21.5 hours.

Samples 12 and 13 were placed on a roller bed at room temperature and at 50 rpm for ca. 23 hours.

Samples 14 and 15 were placed on a roller bed at room temperature and at 50 rpm for ca. 25 hours.

Results After ca. 21.5/23/25 Hour Periods

At the end of the specified rolling period the pH of each sample was measured and a visual observation of each sample was made using a light box as described in European Pharmacopoeia Method 2.9.20 (above), inspecting the samples against a black and a white background. The sample was also tested by illumination using a narrow (Tyndall) beam light source and then visually inspected from a direction perpendicular to the light beam in order to identify undissolved solid particles.

| Sample # | pH |
| --- | --- |
| 1 | 4.09 |
| 2 | 3.71 |
| 3 | 3.47 |
| 4 | 4.08 |
| 5 | 3.75 |
| 6 | 3.37 |
| 7 | 3.03 |
| 8 | 2.83 |
| 9 | 3.81 |
| 10 | 3.48 |
| 11 | 2.81 |
| 12 | 3.31 |
| 13 | 3.24 |
| 14 | N = 1 3.27 |
|  | N = 2 3.28 |
|  | N = 3 3.28 |
| 15 | N = 1 3.26 |
|  | N = 2 3.26 |
|  | N = 3 3.27 |

Visual Assessment

| Sample # | Visual Appearance |
| --- | --- |
| 1 | Not in Solution |
| 2 | Not in Solution |
| 3 | Clear |
| 4 | Not in Solution |
| 5 | Not in Solution |
| 6 | Clear |
| 7 | Clear |
| 8 | Clear |
| 9 | Not in Solution |
| 10 | Clear |
| 11 | Clear |
| 12 | Haze Present |
| 13 | Haze Present |
| 14 | N = 1 Clear |
|  | N = 2 Clear |
|  | N = 3 Clear |
| 15 | N = 1 Clear |
|  | N = 2 Clear |
|  | N = 3 Clear |

The following observations were made:

Samples 7, 8 & 11 appeared to have become solutions within 2 hours of being placed on the roller bed Sample 6 appeared to have become a solution within 4 hours of being placed on the roller bed Samples 3 and 10 appeared to have become a solution within 20 hours of being placed on the roller bed.

Conclusion

After the ca. 24 hour period it can be concluded that to achieve a clear solution the solution concentration of 1-(4-{[4-(dimethylamino)piperidin-1-yl]carbonyl}phenyl)-3-[4-(4,6-dimorpholin-4-yl-1,3,5-triazin-2-yl)phenyl]urea must be less than 6 mg/ml and more than 2.5 mole equivalents of DL-lactic acid must be used in the formulation. However, the results above for Samples 14 and 15 show that clear solutions are achievable at a solution concentration of 1-(4-{[4-(dimethylamino)piperidin-1-yl]carbonyl}phenyl)-3-[4-(4,6-dimorpholin-4-yl-1,3,5-triazin-2-yl)phenyl]urea of both 6 mg/ml and 6.5 mg/ml with 3.6 and 3.7 mole equivalents, respectively, of DL-lactic acid. These results for Samples 14 and 15, when compared with those for Samples 12 and 13, reflect the fact a metastable zone likely exists in which both clear and non-clear solutions may result.

Results After 72 Hour Period

After the ca. 21.5 hour rolling periods above, Samples 1-11 were stored at room temperature without rolling for further time to provide a total experimental period of ca. 72 hours. It was observed that some samples became a solution at the end of the total 72 hour period that were not in solution after the initial ca. 21.5 hour rolling period.

After the ca. 25 hour rolling periods above, Samples 14 and 15 were stored with rolling at room temperature for further time to provide a total experimental period of ca. 73 hours.

These samples were visually assessed made using a light box as described in European Pharmacopoeia Method 2.9.20 (above), inspecting the samples against a black and a white background. The sample was also tested by illumination using a narrow (Tyndall) beam light source and then visually inspected from a direction perpendicular to the light beam in order to identify undissolved solid particles. The pH was also measured. The results were as follows:

(i) Visual Assessment After 72 Hours

| Sample # | Visual Appearance |
| --- | --- |
| 1 | Not in Solution |
| 2 | Haze Present |
| 3 | Clear |
| 4 | Not in Solution |
| 5 | Clear |
| 6 | Clear |
| 7 | Clear |
| 8 | Clear |
| 9 | Clear |
| 10 | Clear |
| 11 | Clear |
| 14 | N = 1 Clear |
|  | N = 2 Clear |
|  | N = 3 Clear |
| 15 | N = 1 Clear |
|  | N = 2 Clear |
|  | N = 3 Clear |

(ii) Comparison of pH Results and Visual Assessments After ca. 24 Hour and 72 Hour Periods

| Sample Number | Concentration (mg/mL) | Target/Actual Mole Equivalence | Buffer pH | pH ca. 24 hours | pH 72 hours | Visual Assessment 24 hours | Visual Assessment 72 hours |
|---|---|---|---|---|---|---|---|
| 1 | 3 | 0.9/0.8 | 3.14 | 4.09 | 4.12 | Not in Solution | Not in Solution |
| 2 | 3 | 2.25/2.5 | 2.86 | 3.71 | 7.31 | Not in Solution | Haze Present |
| 3 | 3 | 3.7/3.7 | 2.69 | 3.47 | 3.41 | Clear | Clear |
| 4 | 5 | 0.9/0.9 | 2.99 | 4.08 | 4.11 | Not in Solution | Not in Solution |
| 5 | 5 | 2.25/2.3 | 2.68 | 3.75 | 3.74 | Not in Solution | Clear |
| 6 | 5 | 3.7/3.8 | 2.55 | 3.37 | 3.35 | Clear | Clear |
| 7 | 5 | 7.2/7.0 | 2.41 | 3.03 | 2.98 | Clear | Clear |
| 8 | 5 | 10.8/10.8 | 2.3 | 2.83 | 2.78 | Clear | Clear |
| 9 | 5.5 | 2.25/2.3 | 2.67 | 3.81 | 3.75 | Not in Solution | Clear |
| 10 | 5.5 | 3.7/3.7 | 2.56 | 3.48 | 3.41 | Clear | Clear |
| 11 | 5.5 | 10.8/11.2 | 2.27 | 2.81 | 2.75 | Clear | Clear |
| 12 | 6.0 | 3.7/3.6 | 2.55 | 3.31 | — | Haze present | — |
| 13 | 6.5 | 3.7/3.9 | 2.50 | 3.24 | — | Haze present | — |
| 14 | 6.0 | 3.7/3.6 | 2.50 | N = 1 3.27, N = 2 3.28, N = 3 3.28 | N = 1 3.26, N = 2 3.24, N = 3 3.27 | N = 1 Clear, N = 2 Clear, N = 3 Clear | N = 1 Clear, N = 2 Clear, N = 3 Clear |
| 15 | 6.5 | 3.7/3.7 | 2.45 | N = 1 3.26, N = 2 3.26, N = 3 3.27 | N = 1 3.25, N = 2 3.26, N = 3 3.29 | N = 1 Clear, N = 2 Clear, N = 3 Clear | N = 1 Clear, N = 2 Clear, N = 3 Clear |

Conclusion

After the total 72 hour experimental period it may be concluded that a clear solution is achievable using a solution concentration of 5 and 5.5 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea where at least 2.3 mole equivalents of DL-lactic acid are used in the formulation. A clear solution is also achievable using a solution concentration of 3 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea where above 2.5 mole equivalents of DL-lactic acid are used in the formulation. The results above for Samples 14 and 15 show that clear solutions are achievable at a solution concentration of 1-(4-{[4-(dimethylamino)piperidin-1-yl]carbonyl}phenyl)-3-[4-(4,6-dimorpholin-4-yl-1,3,5-triazin-2-yl)phenyl]urea of both 6 mg/ml and 6.5 mg/ml with 3.6 and 3.7 mole equivalents, respectively, of DL-lactic acid. These results for Samples 14 and 15, when compared with those for Samples 12 and 13, reflect the fact a metastable zone likely exists in which both clear and non-clear solutions may result.

4. Investigation Regarding 3 mg/ml Aqueous Formulations of 1-(4-{[4-(dimethylamino)piperidin-1-yl]carbonyl}phenyl)-3-[4-(4,6-dimorpholin-4-yl-1,3,5-triazin-2-yl)phenyl]urea with 6.8 Mole Equivalents of Orthophosphoric Acid Procedure A ca. 33.3 mM aqueous orthophosphoric acid solution was prepared as follows. 0.32569 g of orthophosphoric acid was dispensed into ca. 80 mL of water for irrigation. This was made to 100 mL volume using water for irrigation in a volumetric flask and the pH was recorded as 1.92.

A 3 mg/mL concentration of 1-(4-{[4-(dimethylamino)piperidin-1-yl]carbonyl}phenyl)-3-[4-(4,6-dimorpholin-4-yl-1,3,5-triazin-2-yl)phenyl]urea was desired and this had to take account of a drug potency of 97.1%.

A scale of 10 mL was decided upon and therefore the target weight of 1-(4-{[4-(dimethylamino)piperidin-1-yl]carbonyl}phenyl)-3-[4-(4,6-dimorpholin-4-yl-1,3,5-triazin-2-yl)phenyl]urea was 30.9 mg. Three samples of API were prepared using the following weights in each 20 mL vial:

| N = 1 | 30.68 mg |
|---|---|
| N = 2 | 31.21 mg |
| N = 3 | 31.04 mg |

10 mL of the orthophosphoric acid buffer prepared above was dispensed, using an air displacement pipette, into each vial. The vials were each closed with a crimped cap and sealed with protective film.

The samples were placed on a roller bed at room temperature for ca. 19 hours.

These samples were visually assessed using a light box as described in European Pharmacopoeia Method 2.9.20 (above), inspecting the samples against a black and a white background. The sample was also tested by illumination using a narrow (Tyndall) beam light source and then visually inspected from a direction perpendicular to the light beam in order to identify undissolved solid particles. The pH was also measured. The results were as follows:

|  | Visual Assessment | Final pH |
| --- | --- | --- |
| N = 1 | Clear | 2.15 |
| N = 2 | Clear | 2.15 |
| N = 3 | Clear | 2.17 |

Dilutions

Although clear, particle-free solutions had been obtained by the above method, the pH of each sample is too low to be preferred for intravenous administration for which a pH of from 3 to 4.5 is preferred.

The 3 samples were therefore each diluted to 0.5 mg/mL, 0.1 mg/mL and 0.05 mg/mL to identify if the pH increased to a suitable pH for intravenous administration. The diluted samples were placed on a roller bed overnight in order to reach equilibrium. The pH was also measured. The pH of the samples was as follows:

0.5 mg/mL

| N = 1 | 2.64 |
| --- | --- |
| N = 2 | 2.63 |
| N = 3 | 2.64 |

0.1 mg/mL

| N = 1 | 3.19 |
| --- | --- |
| N = 2 | 3.21 |
| N = 3 | 3.20 |

0.05 mg/mL

| N = 1 | 3.47 |
| --- | --- |
| N = 2 | 3.48 |
| N = 3 | 3.49 |

Each of the samples was visually assessed using a light box as described in European Pharmacopoeia Method 2.9.20 (above), inspecting the samples against a black and a white background. The sample was also tested by illumination using a narrow (Tyndall) beam light source and then visually inspected from a direction perpendicular to the light beam in order to identify undissolved solid particles. Each sample was observed to be a visually clear solution.

Conclusion

The results show that it is possible to formulate a clear, particle-free 3 mg/ml aqueous solution formulation of 1-(4-{[4-(dimethylamino)piperidin-1-yl]carbonyl}phenyl)-3-[4-(4,6-dimorpholin-4-yl-1,3,5-triazin-2-yl)phenyl]urea with 6.8 mole equivalents of orthophosphoric acid. However, the pH of this formulation, or a reconstituted formulation thereof, would not be suitable for intravenous administration and therefore it would have to subsequently diluted below 0.5 mg/mL to achieve a solution pH suitable for intravenous administration.

When these results are compared to the results obtained for the lactic acid formulations above, the pH and 1-(4-{[4-(dimethylamino)piperidin-1-yl]carbonyl}phenyl)-3-[4-(4,6-dimorpholin-4-yl-1,3,5-triazin-2-yl)phenyl]urea concentrations achievable are lower when using orthophosphoric acid. Lactic acid is therefore generally more suitable than orthophosphoric acid for the preparation of an aqueous solution formulation for intravenous administration of 1-(4-{[4-(dimethylamino)piperidin-1-yl]carbonyl}phenyl)-3-[4-(4,6-dimorpholin-4-yl-1,3,5-triazin-2-yl)phenyl]urea according to the invention.

5. Investigation Regarding 3 mg/ml, 4 mg/ml and 5 mg/ml Aqueous Formulations of 1-(4-{[4-(dimethylamino)piperidin-1-yl]carbonyl}phenyl)-3-[4-(4,6-dimorpholin-4-yl-1,3,5-triazin-2-yl)phenyl]Urea with Acetic Acid Procedure In order to prepare a 33.3 mM acetic acid solution 0.2071 g of glacial acetic acid was dispensed into a 250 mL glass beaker and approximately 80 mL of WFI (water for irrigation) was added.

0.0138 g of sodium acetate trihydrate was added and dissolved into solution. The solution was made to 100 mL volume in a volumetric flask using WFI and the pH was recorded as 3.35.

Three concentrations of API (3, 4 and 5 mg/mL) were desired which had to be corrected to take account of an API potency of 97.1%. The API weights were determined according to the following calculations.

30 mg active is 30.9 mg 1-(4-{[4-(dimethylamino)piperidin-1-yl]carbonyl}phenyl)-3-[4-(4,6-dimorpholin-4-yl-1,3,5-triazin-2-yl)phenyl]urea 40 mg active is 41.2 mg 1-(4-{[4-(dimethylamino)piperidin-1-yl]carbonyl}phenyl)-3-[4-(4,6-dimorpholin-4-yl-1,3,5-triazin-2-yl)phenyl]urea 50 mg active is 51.49 mg 1-(4-{[4-(dimethylamino)piperidin-1-yl]carbonyl}phenyl)-3-[4-(4,6-dimorpholin-4-yl-1,3,5-triazin-2-yl)phenyl]urea The following weights were dispensed into 20 mL glass vials:

|  | 3 mg/mL | 4 mg/mL | 5 mg/mL |
| --- | --- | --- | --- |
| N = 1 | 30.86 mg | 41.13 mg | 51.49 mg |
| N = 2 | 30.85 mg | 41.12 mg | 51.55 mg |
| N = 3 | 30.76 mg | 41.21 mg | 51.66 mg |

10 mL of the acetic acid buffer prepared above was introduced into each of the weighed samples. The vials were each closed with a crimped cap and sealed with protective film.

The samples were placed on a roller bed at room temperature and visually assessed using a light box as described in European Pharmacopoeia Method 2.9.20 (above), inspecting the samples against a black and a white background. The sample was also tested by illumination using a narrow (Tyndall) beam light source and then visually inspected from a direction perpendicular to the light beam in order to identify undissolved solid particles. The visual analysis was carried out at 24 hour, 48 hour, 72 hour and 6 day periods.

Results

No sample had achieved a clear solution after any of these 24 hour, 48 hour, 72 hour and 6 day periods.

The pH of the samples was assessed as follows:

(a) pH Check after 48 hours

Buffer initial pH=3.35

(i) re. 3 mg/mL Samples

| | |
|---|---|
| N = 1 | 3.88 |
| N = 2 | 3.89 |
| N = 3 | 3.90 |

(ii) re. 4 mg/mL Samples

| | |
|---|---|
| N = 1 | 3.94 |
| N = 2 | 3.95 |
| N = 3 | 3.95 |

(iii) re. 5 mg/mL Samples

| | |
|---|---|
| N = 1 | 3.99 |
| N = 2 | 4.00 |
| N = 3 | 4.00 |

(b) pH Check after 6 Days (i) re. 3 mg/mL Samples

| | |
|---|---|
| N = 1 | 3.99 |
| N = 2 | 3.95 |
| N = 3 | 3.96 |

(ii) re. 4 mg/mL Samples

| | |
|---|---|
| N = 1 | 4.07 |
| N = 2 | 4.03 |
| N = 3 | 4.04 |

(iii) re. 5 mg/mL Samples

| | |
|---|---|
| N = 1 | 4.18 |
| N = 2 | 4.18 |
| N = 3 | 4.19 |

Conclusion

The results show that at 3, 4 and 5 mg/ml concentrations, 1-(4-{[4-(dimethylamino)piperidin-1-yl]carbonyl}phenyl)-3-[4-(4,6-dimorpholin-4-yl-1,3,5-triazin-2-yl)phenyl]urea does not produce a clear solution using 33.3 mM acetic acid. The 3 mg/ml aqueous formulation used contained ca. 6.8 mole equivalents of acetic acid. The 4 mg/ml aqueous formulation used contained ca. 5.1 mole equivalents of acetic acid. The 5 mg/ml aqueous formulation used contained ca. 4.1 mole equivalents of acetic acid.

6. Investigation Regarding 3 and 3.5 mg/ml Aqueous Formulations of 1-(4-{[4-(dimethylamino)piperidin-1-yl]carbonyl}phenyl)-3-[4-(4,6-dimorpholin-4-yl-1,3,5-triazin-2-yl)phenyl]urea with Orthophosphoric Acid A 33.3 mM aqueous orthophosphoric acid solution was prepared as follows. 0.32767 g of orthophosphoric acid was dispensed into ca. 75 mL of water for irrigation. This was made to 100 mL volume using water for irrigation in a volumetric flask and the pH was recorded as 1.94.

3 and 3.5 mg/mL formulations of 1-(4-{[4-(dimethylamino)piperidin-1-yl]carbonyl}phenyl)-3-[4-(4,6-dimorpholin-4-yl-1,3,5-triazin-2-yl)phenyl]urea was desired and this had to take account of a drug potency of 97.1%.

The 3 mg/ml aqueous formulation used contained ca. 6.8 mole equivalents of orthophosphoric acid. The 3.5 mg/ml aqueous formulation used contained ca. 5.9 mole equivalents of orthophosphoric acid.

A scale of 5 mL was decided upon and therefore the target weight of 1-(4-{[4-(dimethylamino)piperidin-1-yl]carbonyl}phenyl)-3-[4-(4,6-dimorpholin-4-yl-1,3,5-triazin-2-yl)phenyl]urea was 15.5 mg for the 3 mg/mL formulation and 18.0 mg for the 3.5 mg/mL formulation. Three samples were prepared for each formulation using the following weights in each 20 mL vial:

| | 3 mg/mL | 3.5 mg/mL |
|---|---|---|
| N = 1 | 15.48 mg | 18.32 mg |
| N = 2 | 16.15 mg | 18.02 mg |
| N = 3 | 15.89 mg | 18.28 mg |

5 mL of the orthophosphoric acid buffer prepared above was dispensed, using an air displacement pipette, into each vial. The vials were each closed with a crimped cap and sealed with protective film.

The samples were placed on a roller bed at room temperature for 15 hours.

These samples were visually assessed using a light box as described in European Pharmacopoeia method 2.9.20 (above), inspecting the samples against a black and a white background. The sample was also tested by illumination using a narrow (Tyndall) beam light source and then visually inspected from a direction perpendicular to the light beam in order to identify undissolved solid particles. All solutions were observed to be visually clear. The pH was also measured.

The results were as follows (n.b the ingoing pH of the 33.3 mM orthophosphoric acid was pH=1.94)

3 mg/mL

| | |
|---|---|
| N = 1 | 2.02 |
| N = 2 | 2.03 |
| N = 3 | 2.05 |

3.5 mg/mL

| | |
|---|---|
| N = 1 | 2.09 |
| N = 2 | 2.07 |
| N = 3 | 2.07 |

Conclusion

The results show that it is possible to formulate a clear, particle-free 3.0 or 3.5 mg/mL aqueous solution formulation of 1-(4-{[4-(dimethylamino)piperidin-1-yl]carbonyl}phenyl)-3-[4-(4,6-dimorpholin-4-yl-1,3,5-triazin-2-yl)phenyl]urea with 5.9 mole equivalents of orthophosphoric acid.

However, the pH readings demonstrate that dilution would be required to provide a suitable pH to allow direct intravenous or parenteral administration of these formulations.

When these results are compared to the results obtained for the lactic acid formulations above, the pH and 1-(4-{[4-(dimethylamino)piperidin-1-yl]carbonyl}phenyl)-3-[4-(4,6-dimorpholin-4-yl-1,3,5-triazin-2-yl)phenyl]urea concentrations achievable are lower when using orthophosphoric acid. Lactic acid is therefore preferable for the preparation of a clear, particle-free aqueous solution formulation of 1-(4-{[4-(dimethylamino)piperidin-1-yl]carbonyl}phenyl)-3-[4-(4,6-dimorpholin-4-yl-1,3,5-triazin-2-yl)phenyl]urea that is suitable for intravenous or parenteral administration.

7. Characterisation of the Crystalline Form of 1-(4-{[4-(dimethylamino)piperidin-1-yl]carbonyl}phenyl)-3-[4-(4,6-dimorpholin-4-yl-1,3,5-triazin-2-yl)phenyl]urea L-lactate PXRD Analysis The powder X-ray diffraction (PXRD) analysis was carried out on a Bruker D4 (trade mark) diffractometer using copper radiation (wavelength: 1.5406 Å). The tube voltage and amperage were set to 35 kV and 40 mA, respectively. The divergence slit used was v6 and the scattering slit was set at 0.499 mm. A variable receiving slit was used. Diffracted radiation was detected by a Vantec detector. A theta-two theta continuous scan at 5.4°/min (0.2 sec/0.018° step) from 2.0 to 55° 2θ was used. A corundum standard was analyzed to check the instrument alignment. The data were collected and analysed using Bruker AXS software. The samples were prepared by placing them on a silicon wafer. DIFFRAC.EVA V3.1 software was used to visualize and evaluate the PXRD spectra. The PXRD data files (.raw) were not processed prior to peak searching. Generally, a threshold value of 1.3 and a width value of 0.3 were used to make the preliminary peak assignments. The output of automated assignments was visually checked to ensure validity and adjustments manually made if necessary. Additionally, peaks were manually assigned within the spectra, if appropriate. A peak at 28.1° 2-theta that related to the mounting medium was manually removed from the list.

To perform an X-ray diffraction measurement using the Bragg-Brentano geometry on the Bruker instrument used for measurements reported herein, the sample is typically placed onto a flat silicon plate. The sample powder is pressed by a glass slide or equivalent to ensure a random surface and proper sample height. The sample holder is then placed into the instrument. The incident X-ray beam is directed at the sample, initially at a small angle relative to the plane of the holder, and then moved through an arc that continuously increases the angle between the incident beam and the plane of the holder. The measurement differences associated with such X-ray powder analyses result from a variety of factors including: (a) errors in sample preparation (e.g., sample height), (b) instrument errors (e.g. flat sample errors), (c) calibration errors, (d) operator errors (including those errors present when determining the peak locations), and (e) the nature of the material (e.g. preferred orientation and transparency errors). Calibration errors and sample height errors often result in a shift of all the peaks in the same direction. Small differences in sample height when using a flat holder will lead to large displacements in the PXRD peak positions. A systematic study showed that, using a Shimadzu XRD-6000 in the typical Bragg-Brentano configuration, a sample height difference of 1 mm leads to peak shifts as high as 1 degree 2-theta (Chen et al.; *J Pharmaceutical and Biomedical Analysis*, 2001; 26, 63). These shifts can be identified from the X-ray diffractogram and can be eliminated by compensating for the shift (applying a systematic correction factor to all peak position values) or recalibrating the instrument. As mentioned above, it is possible to rectify measurements from the various machines by applying a systematic correction factor to bring the peak positions into agreement. In general, this correction factor will bring the measured peak positions from the Bruker into agreement with the expected peak positions and may be in the range of from 0 to 0.2 degree 2-theta.

The PXRD pattern of the crystalline form of 1-(4-{[4-(dimethylamino)piperidin-1-yl]carbonyl}phenyl)-3-[4-(4,6-dimorpholin-4-yl-1,3,5-triazin-2-yl)phenyl]urea L-lactate of Example 4, Preparation A, is provided in FIG. 1 and is characterized by the following peak listing that is expressed in terms of the degree 2θ (±0.2 degrees 2-theta) and relative intensity (of ≥2.5%) as measured on a Bruker D4 diffractometer with copper K-alpha (CuKα) radiation:

| Angle (degree 2θ) | Relative intensity (%)* |
|---|---|
| 6.5 | 5.9 |
| 9.2 | 9.7 |
| 11.0 | 13.2 |
| 13.0 | 15.8 |
| 13.3 | 4.3 |
| 13.7 | 2.9 |
| 15.6 | 9.4 |
| 15.9 | 17.2 |
| 16.2 | 28.8 |
| 17.0 | 17.7 |
| 17.3 | 43.9 |
| 18.4 | 46 |
| 18.9 | 51.3 |
| 19.1 | 20 |
| 19.9 | 54.6 |
| 20.9 | 67.1 |
| 22.1 | 19.5 |
| 22.5 | 8.4 |
| 22.9 | 10.3 |
| 23.1 | 100 |
| 24.2 | 2.6 |
| 25.0 | 18.1 |
| 25.6 | 15.8 |
| 26.3 | 4.8 |
| 26.6 | 10.2 |
| 28.2 | 9.8 |
| 28.5 | 10.8 |
| 29.2 | 2.7 |
| 30.3 | 4.3 |
| 30.7 | 4.2 |
| 35.1 | 2.9 |

(*The relative intensities may change depending on the crystal size and morphology)

This crystalline form of 1-(4-{[4-(dimethylamino)piperidin-1-yl]carbonyl}phenyl)-3-[4-(4,6-dimorpholin-4-yl-1,3,5-triazin-2-yl)phenyl]urea L-lactate is distinguished from other known (semi-crystalline) forms of this salt by having characterizing peaks at about 6.5, 15.9, 20.9, 22.1 and 23.1 degrees 2-theta (±0.2 degrees 2-theta).

7. Chemical Stability of a Lyophilised Solid Formulation of the Invention

Samples of a lyophilised solid formulation prepared in accordance with the method of Example 2 in 50 mL clear vials were analysed for chemical degradation after storage at 25° C./60% Relative Humidity (RH) and 40° C./75% RH at a variety of different timepoints. Several samples were evaluated for each condition to allow representative results at the selected timepoints.

The 40° C./75% RH samples were tested after 6 months.

The 25° C./60% RH samples were tested after 6 months, 12 months, 24 months and 36 months.

The samples were tested for chemical purity using High Performance Liquid Chromatography (HPLC) using the following methodology in order to measure any degradation during the period of testing.

HPLC Method

The solutions, samples and standards for use in the HPLC method are prepared as below:

Reference Standard: 1-(4-{[4-(dimethylamino)piperidin-1-yl]carbonyl}phenyl)-3-[4-(4,6-dimorpholin-4-yl-1,3,5-triazin-2-yl)phenyl]urea with a known potency value.

Diluent: Acetonitrile/Water (1:1 v/v).

Mobile Phase A: 10 mM aqueous ammonium bicarbonate buffer solution with pH adjusted to 9.8 with aqueous ammonium hydroxide solution Mobile Phase B: Acetonitrile Sample solvent: Add 3 mL of 0.1N aqueous hydrochloric acid into a 1000 mL volumetric flask and dilute to set volume with the Diluent (Acetonitrile/water, 1:1 v/v). Mix well.

Note: larger or smaller volumes of solutions may be prepared using the appropriate ratio of components.

Standard and Check Standard Preparations:

Accurately prepare two solutions of ca. 2 mg/mL (±10%) of 1-(4-{[4-(dimethylamino)piperidin-1-yl]carbonyl}phenyl)-3-[4-(4,6-dimorpholin-4-yl-1,3,5-triazin-2-yl)phenyl]urea Reference Standard in Sample solvent, and record the concentrations accurately of both. These are the Standard and Check standard solutions. Produce Standard and Check standard preparations by accurately diluting these solutions to a concentration of around 2 microgram/mL of 1-(4-{[4-(dimethylamino)piperidin-1-yl]carbonyl}phenyl)-3-[4-(4,6-dimorpholin-4-yl-1,3,5-triazin-2-phenyl]urea using the Diluent.

Sensitivity Solution:

Accurately dilute the Standard preparation to a concentration of approximately 0.06 microgram/mL of 1-(4-{[4-(dimethylamino)piperidin-1-yl]carbonyl}phenyl)-3-[4-(4,6-dimorpholin-4-yl-1,3,5-triazin-2-phenyl]urea using the Diluent.

Sample Preparation:

Reconstitute two lyophilised solid formulation vials of 1-(4-{[4-(dimethylamino)piperidin-1-yl]carbonyl}phenyl)-3-[4-(4,6-dimorpholin-4-yl-1,3,5-triazin-2-yl)phenyl]urea (prepared in accordance with the method of Example 2) by adding 20 mL of water to each vial, shaking the vial to dissolve the solid and wait for the bubbles to disappear. Transfer the solution into a 1000 mL volumetric flask. Rinse each vial at least twice with Diluent and transfer the washings into the volumetric flask. Dilute to the set volume with Diluent.

Chromatographic Conditions:

Liquid chromatographic system—e.g. Waters 2695 (trade mark) or Agilent 1100 (trade mark) machine Column: Waters Xbridge C18 (trade mark), 15 cm×4.6 mm, 3.5 µm or equivalent Column Temperature: 40° C.

Injection Volume: 20 µL

Flow Rate: 1.0 mL/min.

Detection: UV at 303 nm

Run Time: 60 minutes

Mobile Phase A

Mobile Phase B

Linear Gradient Table:

| Time (minutes) | % Mobile Phase A | % Mobile Phase B |
| --- | --- | --- |
| 0 | 90 | 10 |
| 37 | 50 | 50 |
| 47 | 10 | 90 |
| 52 | 10 | 90 |
| 53 | 90 | 10 |
| 60 | 90 | 10 |

Explanatory Notes

Prepare the HPLC machine by pumping Mobile Phase B through the column until a stable baseline is obtained (this usually takes around 30 minutes). Re-equilibrate the chromatographic system with Mobile Phase A (usually 10-15 minutes) before running the injection sequence.

Prior to running samples, ensure that the system is suitable for use by injecting blank diluent, sensitivity solution and standard preparation using the chromatographic conditions above.

The following criteria must be satisfied on initial HPLC set-up or after any significant change to the system. It is recommended to inject at least one conditioning blank prior to testing system suitability.

Figure 3:
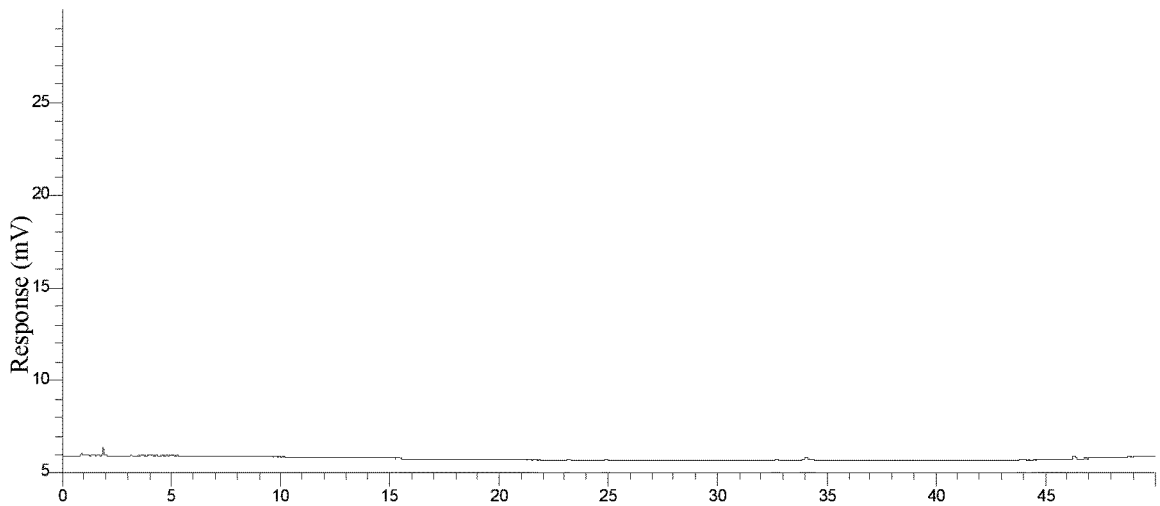
FIG. 3 shows a chromatogram of blank solution (diluent) at full scale.
Figure 4:
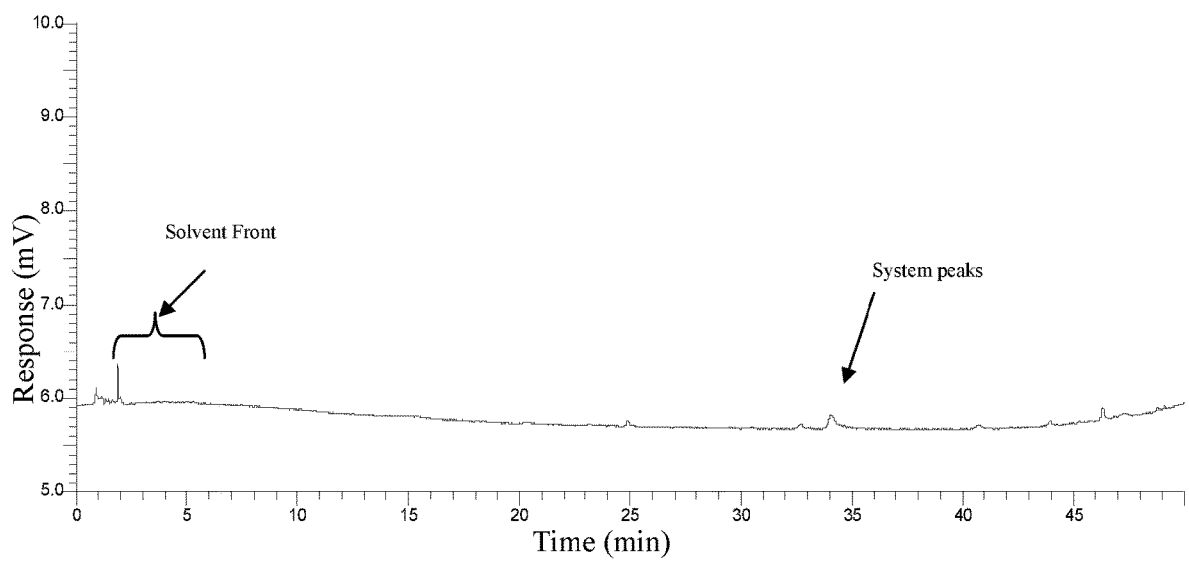
FIG. 4 shows an expanded chromatogram of blank solution (diluent).

| Test | # of Injections | Solution | Criteria |
| --- | --- | --- | --- |
| Blank | 1 | Diluent | Chromatogram similar to FIGS. 3 and 4 |
| Signal to Noise | 1 | Sensitivity Solution | European Pharmacopoeia (EP)/United States Pharmacopoeia (USP) Signal to Noise ≥ 10 |
| Repeatability | 5 | Standard preparation | Relative Standard Deviation ≤ 5.0% |
| Retention time | 1* | | 28-36 minutes |
| Efficiency (Plate)** | | | Plate number for 1-(4-{[4-(dimethylamino)piperidin-1-yl]carbonyl}phenyl)-3-[4-(4,6-dimorpholin-4-yl-1,3,5-triazin-2-yl)phenyl]urea peak ≥ 10,000 |
| Peak Asymmetry (T)** | | | 0.9 ≤ T ≤ 2.0 for 1-(4-{[4-(dimethylamino)piperidin-1-yl]carbonyl}phenyl)-3-[4-(4,6-dimorpholin-4-yl-1,3,5-triazin-2-yl)phenyl]urea peak |

*Use average of all system suitability (repeatability) injections.
**Refer to United States Pharmacopoeia (USP) calculation equations for Efficiency and Peak Asymmetry.

Inject the check standard preparation according to the chromatographic conditions above. The response factor (calculated from the area, standard weight, dilution factor and purity factor of the standard) of this check standard preparation must be within ±5% of the standard preparation.

After the system suitability has been demonstrated, inject the blank solution, standard preparation and prepared test samples, followed by an injection of the standard preparation, according to the chromatographic conditions above. It is recommended that no more than 6 test samples be injected between standard preparation injections. For each injection (standard and sample), measure the retention time and area of the 1-(4-{[4-(dimethylamino)piperidin-1-yl]carbonyl}phenyl)-3-[4-(4,6-dimorpholin-4-yl-1,3,5-triazin-2-phenyl]urea peak in each chromatogram. For each sample injection, also measure the retention times and peak area of any peaks present in the sample injection that do not appear in the blank injection. Do not integrate gradient artifacts, if present. Compare the blank injection chromatogram to the sample chromatogram to determine which peaks in the sample are related to the blank and gradient artifact peaks. Calculate the % degradants and report the individual degradant peaks which are at or above 0.05%.

Unknown degradants should be reported individually by their relative retention time. Known degradants should be reported individually by name.

The results are summarised in the tables below.

Key

NMT=Not More Than.

NR=Not Reported.

RRT=Relative Retention Time

All % are w/w

Degradant 1

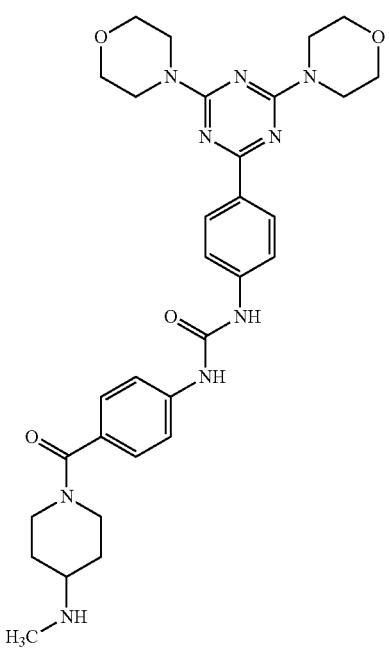 [SMILES: CNC1CCN(C(=O)c2ccc(NC(=O)Nc3ccc(-c4nc(N5CCOCC5)nc(N5CCOCC5)n4)cc3)cc2)CC1]

Degradant 2

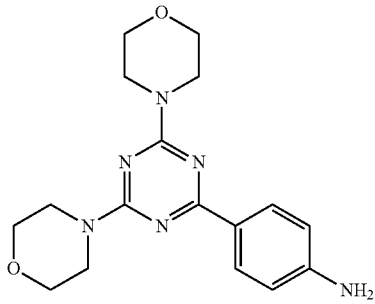 [SMILES: Nc1ccc(-c2nc(N3CCOCC3)nc(N3CCOCC3)n2)cc1]

Degradants 3, 4, 5 and 6

These were each characterised by their RRT only.

| Timepoint | Acceptance criteria | Initial | 25° C./60% RH | | | |
|---|---|---|---|---|---|---|
| | | | 6 months | 12 months | 24 months | 36 months |
| Degradant 1 | NMT 1.1% | 0.74% | 0.77% | 0.77% | 0.79% | 0.87% |
| Degradant 2 | NMT 0.5% | NMT 0.05% | NMT 0.05% | NMT 0.05% | NMT 0.05% | NMT 0.05% |
| Degradant 3 RRT 0.86 | NMT 0.5% each | 0.10% | 0.09% | 0.10% | 0.08% | NR* |
| Degradant 4 RRT 1.05 | NMT 0.5% each | NMT 0.05% | NMT 0.05% | 0.06% | NMT 0.05% | NMT 0.05% |
| Degradant 5 RRT 1.15 | NMT 0.5% each | NMT 0.05% | NMT 0.05% | 0.07% | 0.06% | NR* |
| Degradant 6 RRT 1.42 | NMT 0.5% each | 0.12% | 0.12% | 0.11% | 0.12% | NR* |
| Total Degradants | NMT 3.0% | 0.96% | 0.98% | 1.1% | 1.1% | 0.87%* |

Degradants 3, 5 and 6 were identified as process related impurities which did not change on stability, and so were not reported at the 36 month timepoint.

| Timepoint | Acceptance criteria | Initial | 40° C./75% RH 6 months |
|---|---|---|---|
| Degradant 1 | NMT 1.1% | 0.74% | 0.80% |
| Degradant 2 | NMT 0.5% | NMT 0.05% | NMT 0.05% |
| Degradant 3 RRT 0.86 | NMT 0.5% each | 0.10% | 0.09% |
| Degradant 6 RRT 1.42 | NMT 0.5% each | 0.12% | 0.12% |
| Total Degradants | NMT 3.0% | 0.96% | 1.0% |

Conclusion

The results show that samples of a lyophilised solid formulation prepared in accordance with the method of Example 2 in a 50 mL clear vial are chemically stable for at least 36 months at 25° C./60% RH and for at least 6 months at 40° C./75% RH.

The invention claimed is:

1. A method of treating cancer in a mammal, comprising administering to said mammal an effective amount of a second pharmaceutical aqueous solution formulation obtained as a clear solution by reconstitution or constitution a lyophilized formulation, said lyophilized formulation obtained by freeze drying a first pharmaceutical aqueous solution formulation comprising:

1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid and water, wherein said 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 6 mg/ml and sufficient lactic acid is present to provide a clear solution.

2. The method of claim 1, wherein said 1-(4-{[4-(dimethylamino)piperidin-1-yl]carbonyl}phenyl)-3-[4-(4,6-dimorpholin-4-yl-1,3,5-triazin-2-yl)phenyl]urea is present in the first pharmaceutical aqueous solution formulation at a solution concentration of from 5.0 to 5.5 mg/ml and at least 2.5 mole equivalents of lactic acid are present.

3. The method of claim 1, wherein said 1-(4-{[4-(dimethylamino)piperidin-1-yl]carbonyl}phenyl)-3-[4-(4,6-dimorpholin-4-yl-1,3,5-triazin-2-yl)phenyl]urea is present in the first pharmaceutical aqueous solution formulation at a solution concentration of about 5 mg/ml, and at least 2.5 mole equivalents of lactic acid are present.

4. The method of claim 1, wherein said 1-(4-{[4-(dimethylamino)piperidin-1-yl]carbonyl}phenyl)-3-[4-(4,6-dimorpholin-4-yl-1,3,5-triazin-2-yl)phenyl]urea is present in said first pharmaceutical aqueous solution formulation at a solution concentration of about 5 mg/ml, and at least 1.5 mole equivalents of lactic acid are present and in an amount sufficient to ensure a clear solution is formed.

5. The method of claim 1, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present in said first pharmaceutical aqueous solution formulation at a solution concentration of about 5 mg/ml, and about 4.1 mole equivalents of lactic acid are present and in an amount sufficient to ensure a clear solution is formed with a pH of no greater than 3.7.

6. The method of claim 1, wherein said 1-(4-{[4-(dimethylamino)piperidin-1-yl]carbonyl}phenyl)-3-[4-(4,6-dimorpholin-4-yl-1,3,5-triazin-2-yl)phenyl]urea is present in said first pharmaceutical aqueous solution formulation at a solution concentration of from 2.5 to 5.5 mg/ml, and from above 2.5 to 8.0 mole equivalents of lactic acid are present and in an amount sufficient to ensure a clear solution is formed.

7. The method of any of claims 1 and 2-6 wherein DL-lactic acid, L-lactic acid or D-lactic acid is used in the first pharmaceutical aqueous solution formulation.

8. The method of any of claims 1 and 2-6, wherein the cancer is selected from leukemia, skin cancer, bladder cancer, breast cancer, uterus cancer, ovary cancer, prostate cancer, lung cancer, colon cancer, pancreas cancer, renal cancer, gastric cancer and brain cancer.

9. The method of claim 8 wherein the cancer is breast cancer.

10. The method of claim 8 wherein the cancer is prostate cancer.

\* \* \* \* \*